(12) United States Patent
Nahm et al.

(10) Patent No.: US 10,696,621 B2
(45) Date of Patent: Jun. 30, 2020

(54) CHIRAL PHASE-TRANSFER CATALYST AND METHOD FOR PREPARING ALPHA-AMINO ACID BY USING THE SAME

(71) Applicant: Research Cooperation Foundation of Yeungnam University, Gyeongsan-si (KR)

(72) Inventors: Kee Pyung Nahm, Gyeongsan-si (KR); Yeon Ji Lee, Daegu (KR); Bae Geun Lim, Daegu (KR); Seung A Woo, Daegu (KR); Ji Inn Oh, Daegu (KR); Won Gyoung Son, Goryeong-gun (KR)

( * ) Notice: Subject to any disclaimer, the term of this patent is extended or adjusted under 35 U.S.C. 154(b) by 0 days.

(21) Appl. No.: 16/302,618

(22) PCT Filed: Feb. 6, 2017

(86) PCT No.: PCT/KR2017/001270
§ 371 (c)(1),
(2) Date: Nov. 16, 2018

(87) PCT Pub. No.: WO2017/200184
PCT Pub. Date: Nov. 23, 2017

(65) Prior Publication Data
US 2019/0292133 A1    Sep. 26, 2019

(30) Foreign Application Priority Data

May 19, 2016  (KR) .................. 10-2016-0061292
Nov. 30, 2016  (KR) .................. 10-2016-0160908

(51) Int. Cl.
| C07C 227/18 | (2006.01) |
| B01J 31/02 | (2006.01) |
| C07D 471/08 | (2006.01) |
| C07D 453/04 | (2006.01) |

(52) U.S. Cl.
CPC .............. *C07C 227/18* (2013.01); *B01J 31/02* (2013.01); *B01J 31/0239* (2013.01); *C07D 453/04* (2013.01); *C07D 471/08* (2013.01); *B01J 2231/4205* (2013.01); *B01J 2231/44* (2013.01); *B01J 2531/002* (2013.01)

(58) Field of Classification Search
USPC ........................................ 562/575
See application file for complete search history.

(56) References Cited

FOREIGN PATENT DOCUMENTS

| KR | 20030044364 A | 6/2003 |
| KR | 20110005470 A | 1/2011 |

OTHER PUBLICATIONS

Ashokkumar, V. et al., "A new class of bifunctional chiral phase transfer catalysts for highly enantioselective asymmetric epoxidation of a,b-unsaturated ketones at ambient temperature", Journal of Molecular Catalysis A: Chemical, [Electronic publishing] Aug. 21, 2015, vol. 409, pp. 127-136.

Islam, M. R. et al., "Synthesis of chiral polymers containing thioetherified cinchonidinium repeating units and their application to asymmetric catalysis", Tetrahedron: Asymmetry, 2014, vol. 25, Nos. 18/19, pp. 1309-1315.

Ooi, T. et al., "Recent Advances in Asymmetric Phase-Transfer Catalysis", Angew. Chem. Int. Ed., 2007, vol. 46, No. 23, pp. 4222-4266.

*Primary Examiner* — Ana Z Muresan
(74) *Attorney, Agent, or Firm* — Eugene H. Nahm

(57) ABSTRACT

The present invention relates to a novel chiral phase-transfer catalyst, and a method for preparing an alpha-amino acid by using the same. According to the present invention, an alpha-amino acid of high optical purity could be synthesized in a high yield under an easy industrially applicable reaction condition by using a novel cinchona alkaloid compound as a chiral phase-transfer catalyst, and thus the present invention can be used as a key technique of the asymmetric alpha-amino acid synthesis and preparation field.

7 Claims, No Drawings

CHIRAL PHASE-TRANSFER CATALYST AND METHOD FOR PREPARING ALPHA-AMINO ACID BY USING THE SAME

TECHNICAL FIELD

The present invention relates to a novel chiral phase-transfer catalyst and a method for preparing an alpha-amino acid using the same.

BACKGROUND ART

Optically active alpha-amino acids and derivatives thereof are widely used in living bodies. Recently, a method of synthesizing an amino acid through a phase transfer reaction using a quaternary ammonium salt as a phase transfer catalyst has attracted great attention as a synthesis method for mass production of these. In particular, by using an ammonium salt derived from a chiral alkaloid as a catalyst, asymmetric synthesis of an optically active alpha-amino acid has become possible. M. J. O'Donnell first reported an asymmetric synthesis method for alpha-amino acids using a compound of Formula A as a chiral phase-transfer catalyst, which is a tetraalkylammonium halide derived from a cinchona alkaloid, which is a chiral alkaloid (O'Donnell, M. J.; Bennett, W. D.; Wu, S. J. Am. Chem. Soc. 1989, 111, 2353). However, in the reaction using the compound of the following formula A as a catalyst, the alpha-amino acid product has an optical purity of only about 80% ee, which has a limitation in terms of mass production.

A

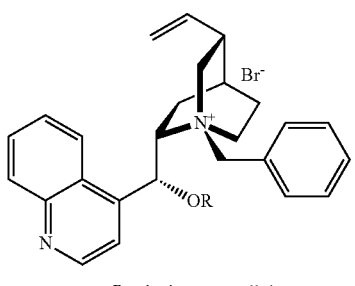

R = hydrogen or allyl

Lygo group [Lygo, B.; Wainwright, P. G. Tetrahedron Lett. 1997, 38, 8595.] and Corey Group [Corey, E. J.; Xu, F.; Noe, M. C. J. Am. Chem. Soc. 1997, 119, 12414.] developed a compound of Formula B as seen below which was a new cinchona alkaloid-based catalyst, and synthesized asymmetric alpha-amino acids through alkylation using the compound as a phase transfer catalyst. Thereafter, Lygo group and Corey group faced an economic issue of high production cost, and because the temperature condition for the alpha-amino acid synthesis was −78° C., its practical industrial application was limited.

B

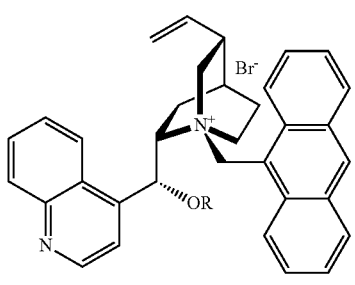

R = hydrogen or allyl

Moreover, the Park Group [Park, H.-G.; Jeong, B.-S.; Yoo, M.-S.; Lee, J.-H.; Park, M.-K.; Lee, Y.-J.; Kim, M.-J.; Jew, S.-S. Angew. Chem. Int. Ed. 2002, 41, 3036.] developed a catalyst of Formula C as seen below, asymmetrically synthesized alpha-amino acids using the catalyst as a phase transfer catalyst, but the reaction needed 5 mol % of the catalyst, 5 equivalents of a reaction reagent, and the reaction temperature had to be maintained at 0° C., thus making industrial application difficult.

C

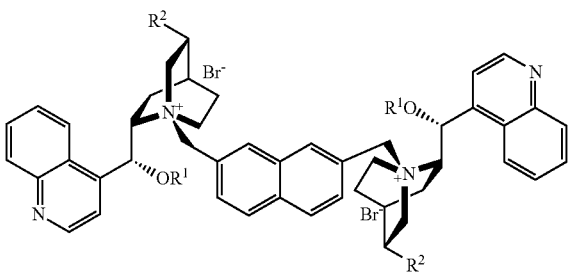

$R^1$ = hydrogen or allyl
$R^2$ = vinyl or ethyl

Under these circumstances, research on the development of a novel chiral phase-transfer catalyst capable of asymmetrically synthesizing alpha-amino acids with high optical purity under industrially applicable reaction conditions has been actively carried out, but it is still inadequate.

INVENTION CONTENT

Technical Problems to be Solved

The present invention is provided to solve the above-described problems, and the inventors have made intensive studies in order to discover new materials that can be used as a chiral phase-transfer catalyst. As a result, the inventors have found novel chiral phase-transfer catalysts derived from cinchona alkaloid which can react with a small amount of the catalyst and equivalents of reagents at room temperature.

Accordingly, an object of the present invention is to provide a novel cinchona alkaloid compound.

Another object of the present invention is to provide a novel use of the cinchona alkaloid compound as a chiral phase-transfer catalyst for asymmetric synthesis of alpha-amino acids.

On the other hand, the technical objects to be solved by the present invention are not limited to the above-identified problems, and other problems which are not mentioned can clearly be understood by persons having ordinary skill in the art from the following description.

Technical Solution

In order to attain the above objects, the present invention provides a cinchona compound represented by Formula 1 below.

[Formula 1]

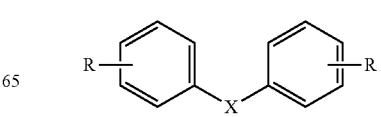

The present invention provides a cinchona alkaloid compound represented by Formula 1 below.

[Formula 1]

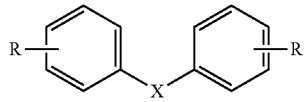

In Formula 1, X represents —CH$_2$—, —C(OH)H—, —C(=O)—, —O—, —S—, —S(=O)— or —S(O$_2$)—;
R represents

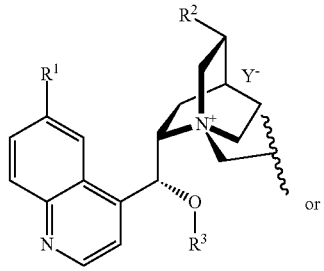

or

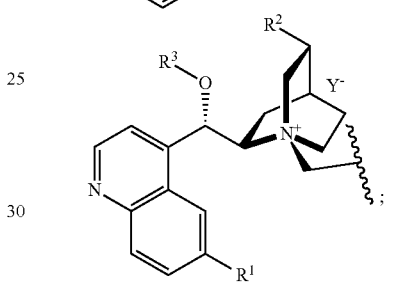

R$^1$ represents hydrogen, C$_1$ to C$_{10}$ alkyl or C$_1$ to C$_5$ alkoxy; R$^2$ represents vinyl or ethyl; R$^3$ represents hydrogen, C$_1$ to C$_{10}$ alkyl, allyl, C$_5$ to C$_{10}$ aryl, naphthalen-1-yl-methyl or anthracen-9-yl-methyl; and Y$^-$ represents a halogen anion selected from the group consisting of fluoride, chloride, bromide and iodide, IO$_4$$^-$, ClO$_4$$^-$, R$^4$SO$_3$$^-$, trifluoromethane sulfonate (OTf$^-$) or HSO$_4$$^-$; and R$^4$ may be C$_1$ to C$_4$ alkyl or C$_5$ to C$_{10}$ aryl.

In this embodiment, "alkyl" refers to linear and branched saturated hydrocarbon groups generally having the indicated number of carbon atoms (e.g., 1 to 10 carbon atoms). Examples of alkyl groups include, but are not limited to, methyl, ethyl, n-propyl, isopropyl, n-butyl, sec-butyl, isobutyl, tert-butyl, n-pentyl, n-hexyl and n-heptyl. If the substitution or branching satisfies the valence requirement, alkyl may be substituted or branched to a parent group or substrate at any ring atom.

"Alkoxy" refers to alkyl —O—, wherein the alkyl is defined as above. Examples of alkoxy groups include, but are not limited to, methoxy, ethoxy and the like. If the substitution or branching satisfies the valence requirement, alkoxy may be substituted or branched to a parent group or substrate at any ring atom. Likewise, if the substitution or branching satisfies the valence requirement, the alkoxy group may include one or more non-hydrogen substituents.

"Aryl" refers to monovalent and divalent aromatic groups, respectively, including 5- and 6-membered monocyclic aromatic groups, and the "heteroaryl" refers to monovalent and divalent aromatic groups, respectively, including 5- and 6-membered monocyclic aromatic groups containing 1 to 4 hetero atoms independently selected from nitrogen, oxygen and sulfur. Examples of monocyclic aryl and heteroaryl groups include, but are not limited to, phenyl, pyridinyl, furanyl, pyrrolyl, thiophenyl, thiazolyl, isothiazolyl, imidazolyl, triazolyl, tetrazolyl, pyrazolyl, oxazolyl, In Formula 1,
X represents —CH$_2$—, —C(OH)H—, —C(=O)—, —O—, —S—, —S(=O)— or —S(O$_2$)—; and
R represents

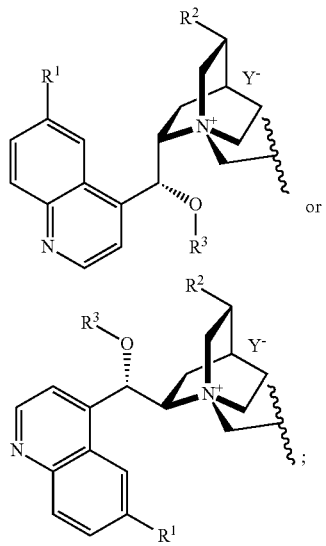

R$^1$ represents hydrogen, C$_1$ to C$_{10}$ alkyl or C$_1$ to C$_5$ alkoxy;
R$^2$ represents vinyl or ethyl;
R$^3$ represents hydrogen, C$_1$ to C$_{10}$ alkyl, allyl, C$_5$ to C$_{10}$ aryl, naphthalen-1-yl-methyl or anthracen-9-yl-methyl;
Y$^-$ represents a halogen anion selected from the group consisting of fluoride, chloride, bromide and iodide, IO$_4$$^-$, ClO$_4$$^-$, R$^4$SO$_3$$^-$, trifluoromethane sulfonate (OTf$^-$) or HSO$_4$$^-$; and
R$^4$ represents C$_1$-C$_4$ alkyl or C$_5$-C$_{10}$ aryl.

The present invention also provides a method of synthesizing an alpha-amino acid using the cinchona alkaloid compound of Formula 1 as a chiral phase-transfer catalyst, a composition for synthesizing an alpha-amino acid, which includes the cinchona alkaloid compound as an active ingredient, and the use of the cinchona alkaloid compound for synthesizing an alpha-amino acid.

In one exemplary embodiment of the present invention, the amino acid synthesis reaction using the catalyst of the present invention may be performed at 10 to 20° C., preferably at room temperature (20° C.) or near room temperature with a high optical purity.

In another exemplary embodiment of the present invention, the chiral phase-transfer catalyst may be used in the range of 0.0005 to 0.012 equivalents or less per equivalent of a reactant, preferably, a high optical purity may be obtained using 0.01 equivalents (1.0% equivalent) or less with respect to one equivalent of the reactant.

Advantageous Effects

A novel cinchona alkaloid compound according to the present invention can be synthesized through a relatively simple process, and when this compound is used as a chiral phase-transfer catalyst, alpha-amino acids can be asymmetrically synthesized with high optical purity under reaction conditions which facilitate industrial application. Therefore, the novel cinchona alkaloid compound of the present invention can be utilized as key technology for fields of synthesis and preparation of alpha-amino acids.

DETAILED DESCRIPTION

Hereinafter, the present invention is described in detail.

isoxazolyl, pyrazinyl, pyridazinyl, pyrimidinyl, and the like. The aryl and heteroaryl groups also include bicyclic and tricyclic groups including the fused 5- and 6-membered ring as defined above. Examples of polycyclic aryl and heteroaryl groups include, but are not limited to, isoquinolinyl, naphthyl, biphenyl, anthracenyl, pyrenyl, carbazolyl, benzoxazolyl, benzodioxazolyl, benzothiazolyl, benzoimidazolyl, benzothiophenyl, quinolinyl, indolyl, benzofuranyl, purinyl, indolizinyl, and the like. If the substitution or branching satisfies the valence requirement, the aryl and heteroaryl groups may be substituted or branched to the parent group or substrate at any ring atom. Likewise, if the substitution or branching satisfies the valence requirement, aryl and heteroaryl groups may contain one or more non-hydrogen substituents. The non-hydrogen substituent of the aryl group and the heteroaryl group may also be substituted with an additional non-hydrogen substituent.

In Formula 1, when X is —$CH_2$—, —$C(OH)H$— or —$C(=O)$—, preferably $R^1$ represents hydrogen or $C_1$-$C_5$ alkoxy; $R^2$ represents vinyl or ethyl; $R^3$ represents hydrogen, $C_1$-$C_{10}$ alkyl, allyl or $C_5$-$C_{10}$ aryl; and $Y^-$ represents a halogen anion selected from the group consisting of fluorine, chlorine, bromine, and iodine.

More preferably, $R^1$ represents hydrogen or methoxy; $R^2$ represents vinyl or ethyl; $R^3$ represents hydrogen or allyl; and $Y^-$ represents a halogen anion selected from the group consisting of fluorine, chlorine, bromine, and iodine, and most preferably, the compound of Formula 1 represents 4,4'-bis(cinchonidium-N-methyl)biphenyl methanone dibromide; 4,4'-bis(O(9)-allyl cinchonidium-N-methyl)biphenyl methanone dibromide; 4,4'-bis(hydrocinchonidium-N-methyl)biphenyl methanone dibromide; 4,4'-bis(O(9)-allyl-hydrocinchonidium-N-methyl)biphenyl methanone dibromide; 3,4'-bis(cinchonidium-N-methyl)biphenyl methanone dibromide; 3,4'-bis(O(9)-allylcinchonidium-N-methyl)biphenyl methanone dibromide; 3,3'-bis(cinchonidium-N-methyl)biphenyl methanone dibromide; 3,3'-bis(O(9)-allyl-cinchonidium-N-methyl)biphenyl methanone dibromide; 4,4'-bis(cinchonidium-N-methyl)biphenyl methane dibromide; 4,4'-bis(O(9)-allylcinchonidium-N-methyl)biphenyl methane dibromide; 4,4'-bis(hydrocinchonidium-N-methyl)biphenyl methane dibromide; 4,4'-bis(O(9)-allylhydrocinchonidium-N-methyl)biphenyl methane dibromide; 4,4'-bis(quinium-N-methyl)biphenyl methane dibromide; 4,4'-bis(O(9)-allylquinium-N-methyl)biphenyl methane dibromide; 4,4'-bis(cinchonidium-N-methyl)biphenyl methanol dibromide; 4,4'-bis(O(9)-allylcinchonidium-N-methyl)biphenyl methanol dibromide; 4,4'-bis(hydrocinchonidium-N-methyl)biphenyl methanol dibromide; 4,4'-bis(O(9)-allyl-hydrocinchonidium-N-methyl)biphenyl methanol dibromide; 4,4'-bis(cinchonium-N-methyl)biphenyl methanone dibromide; 4,4'-bis(O(9)-allylcinchonium-N-methyl)biphenyl methanone dibromide; 4,4'-bis(cinchonium-N-methyl)biphenyl methane dibromide; 4,4'-bis(O(9)-allylcinchonium-N-methyl)biphenyl methane dibromide; 4,4'-bis(quinidium-N-methyl)biphenyl methane dibromide; 4,4'-bis(O(9)-allylquinidium-N-methyl)biphenyl methane dibromide; 4,4'-bis(cinchonium-N-methyl)biphenyl methanol dibromide; or 4,4'-bis(O(9)-allylcinchonium-N-methyl)biphenyl methanol dibromide, but the present invention is not limited thereto.

In addition, In Formula 1, when X is —O—, —S— or —S(=O)—, preferably $R^1$ represents hydrogen or $C_1$-$C_5$ alkoxy; $R^2$ represents vinyl or ethyl; $R^3$ represents hydrogen, $C_1$-$C_{10}$ alkyl, allyl or $C_5$-$C_{10}$ aryl; and $Y^-$ represents a halogen anion selected from the group consisting of fluorine, chlorine, bromine, and iodine.

More preferably, $R^1$ represents hydrogen or methoxy; $R^2$ represents vinyl or ethyl; $R^3$ represents hydrogen, allyl or benzyl; and $Y^-$ represents a halogen anion selected from the group consisting of fluorine, chlorine, bromine, and iodine, and most preferably, the compound of Formula 1 represents 4,4'-bis(cinchonidium-N-methyl)biphenyl ether dibromide; 4,4'-bis(O(9)-allylcinchonidium-N-methyl)biphenyl ether dibromide; 4,4'-bis(O(9)-benzyl-cinchonidium-N-methyl)biphenyl ether dibromide; 4,4'-bis(hydrocinchonidium-N-methyl)biphenyl ether dibromide; 4,4'-bis(O(9)-allyl-hydrocinchonidium-N-methyl)biphenyl ether dibromide; 4,4'-bis(quinium-N-methyl)biphenyl ether dibromide; 4,4'-bis(O(9)-allylquinium-N-methyl)biphenyl ether dibromide; 3,3'-bis(cinchonidium-N-methyl)biphenyl ether dibromide; 3,3'-bis(O(9)-allylcinchonidium-N-methyl)biphenyl ether dibromide; 4,4'-bis(cinchonidium-N-methyl)biphenyl thioether dibromide; 4,4'-bis(O(9)-allylcinchonidium-N-methyl)biphenyl thioether dibromide; 4,4'-bis(hydrocinchonidium-N-methyl)biphenyl thioether dibromide; 4,4'-bis(O(9)-allylhydrocinchonidium-N-methyl)biphenyl thioether dibromide; 4,4'-bis(quinium-N-methyl)biphenyl thioether dibromide; 4,4'-bis(O(9)-allylquinium-N-methyl)biphenyl thioether dibromide; 3,3'-bis(cinchonidium-N-methyl)biphenyl sulfide dibromide; 3,3'-bis(O(9)-allylcinchonidium-N-methyl)biphenyl sulfide dibromide; 4,4'-bis(cinchonidium-N-methyl)biphenyl sulfoxide dibromide; 4,4'-bis(O(9)-allylcinchonidium-N-methyl)biphenyl sulfoxide dibromide; 4,4'-bis(hydrocinchonidium-N-methyl)biphenyl sulfoxide dibromide; 4,4'-bis(O(9)-allylhydrocinchonidium-N-methyl)biphenyl sulfoxide dibromide; 4,4'-bis(cinchonium-N-methyl)biphenyl ether dibromide; 4,4'-bis(O(9)-allylcinchonium-N-methyl)biphenyl ether dibromide; 4,4'-bis(quinidium-N-methyl)biphenyl ether dibromide; 4,4'-bis(O(9)-allylquinidium-N-methyl)biphenyl ether dibromide; 4,4'-bis(cinchonium-N-methyl)biphenyl thioether dibromide; 4,4'-bis(O(9)-allylcinchonium-N-methyl)biphenyl thioether dibromide; 4,4'-bis(quinidium-N-methyl)biphenyl thioether dibromide; 4,4'-bis(cinchonium-N-methyl)biphenyl sulfoxide dibromide; or 4,4'-bis(O(9)-allylcinchonium-N-methyl)biphenyl sulfoxide dibromide, but the present invention is not limited thereto.

In Formula 1, when X is —$S(O_2)$—, preferably $R^1$ represents hydrogen or $C_1$-$C_5$ alkoxy; $R^2$ represents vinyl or ethyl; $R^3$ represents hydrogen, $C_1$-$C_{10}$ alkyl, allyl or $C_5$-$C_{10}$ aryl; and $Y^-$ represents a halogen anion selected from the group consisting of fluorine, chlorine, bromine and iodine.

More preferably, $R^1$ represents hydrogen; $R^2$ represents vinyl or ethyl; $R^3$ represents hydrogen or allyl; and $Y^-$ represents a halogen anion selected from the group consisting of fluorine, chlorine, bromine and iodine.

Most preferably, the compound of Formula 1 represents 4,4'-bis(cinchonidium-N-methyl)biphenyl sulfone dibromide; 4,4'-bis(O(9)-allylcinchonidium-N-methyl)biphenyl sulfone dibromide; 4,4'-bis(hydrocinchonidium-N-methyl)biphenyl sulfone dibromide; 4,4'-bis(O(9)-allylhydrocinchonidium-N-methyl)biphenyl sulfone dibromide; 4,4'-bis(cinchonium-N-methyl)biphenyl sulfone dibromide; or 4,4'-bis(O(9)-allylcinchonium-N-methyl)biphenyl sulfone dibromide, but the present invention is not limited thereto.

Meanwhile, the cinchona alkaloid compound of Formula 1 according to the present invention may be prepared by various methods.

In one exemplary embodiment, as shown in Reaction Scheme 2, a cinchona alkaloid compound represented by Formulas 3, 5, 7, 9, 11, 13 or 15 may be synthesized, respectively, by reacting a compound of Formula 2a, such as (−)-cinchonidine, (−)-hydrocinchonidine, (−)-quinine or (−)-hydroquinine, with bis(4-(bromomethyl)phenyl)methanone, bis(3,4'-(bromomethyl)phenyl)methanone, bis(3-(Bromomethyl)phenyl)methanone, bis(4-(Bromomethyl)phenyl)

methane, bis(4-(bromomethyl)phenyl)methanol, 4,4'-oxybis-(bromomethyl)benzene, bis(4-(bromomethyl)phenyl)sulfane, 4,4'-sulfinylbis(bromomethyl)benzene or 4,4'-sulfonylbis-(bromomethyl)benzene, respectively. In addition, a cinchona alkaloid compound represented by Formula 4, 6, 8, 10, 12, 14 or 16 may be synthesized, respectively, by reacting each of the obtained products with a halogenated compound such as one or more of, various allyl halides, various benzyl halides, or $C_1$-$C_{10}$ alkyl halides under basic conditions.

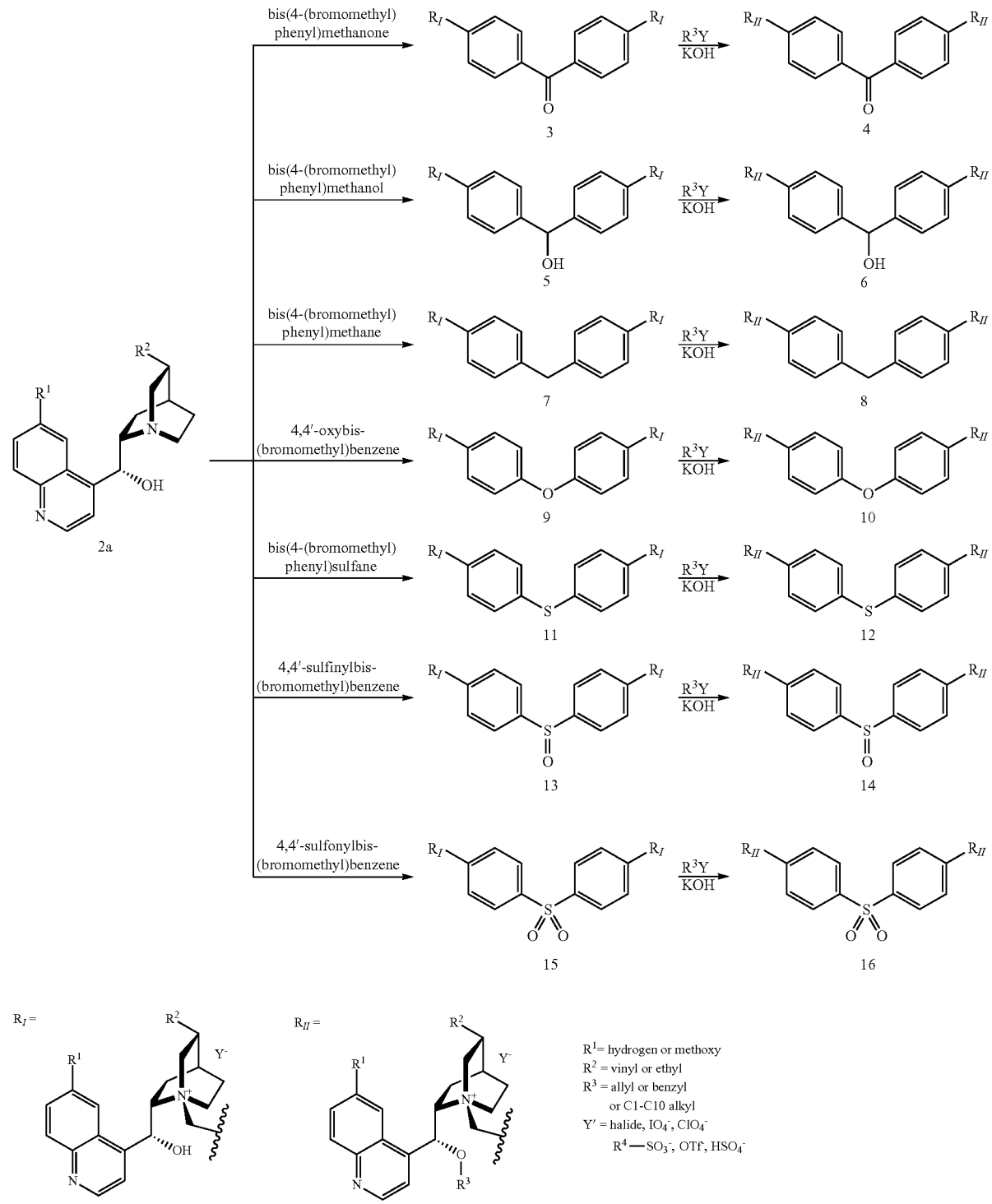

In another aspect, as shown in Reaction Scheme 3, a cinchona alkaloid compound represented by Formula 17, 19, 21, 23, 25, 27 or 29 may be synthesized, respectively, by reacting a compound represented by Formula 2b, such as (+)-cinchonine, (+)-hydrocinchonine, (+)-quinidine or (+)-hydroquinidine, with bis(4-(bromomethyl) phenyl)methanone, bis(4-(bromomethyl)phenyl)methane, bis(4-(bromomethyl)phenyl)methanol, 4,4'-oxybis(bromomethyl) benzene, bis(4-(bromomethyl)phenyl)sulfane, 4,4'-sulfinylbis-(bromomethyl)benzene or 4,4'-sulfonylbis (bromomethyl)benzene. A cinchona alkaloid compound represented by Formula 18, 20, 22, 24, 26, 28 or 30 may be synthesized, respectively, by reacting each of the obtained products with a halogenated compound such as, one or more of, various allyl halides, various benzyl halides, or $C_1$-$C_{10}$ alkyl halides under basic conditions.

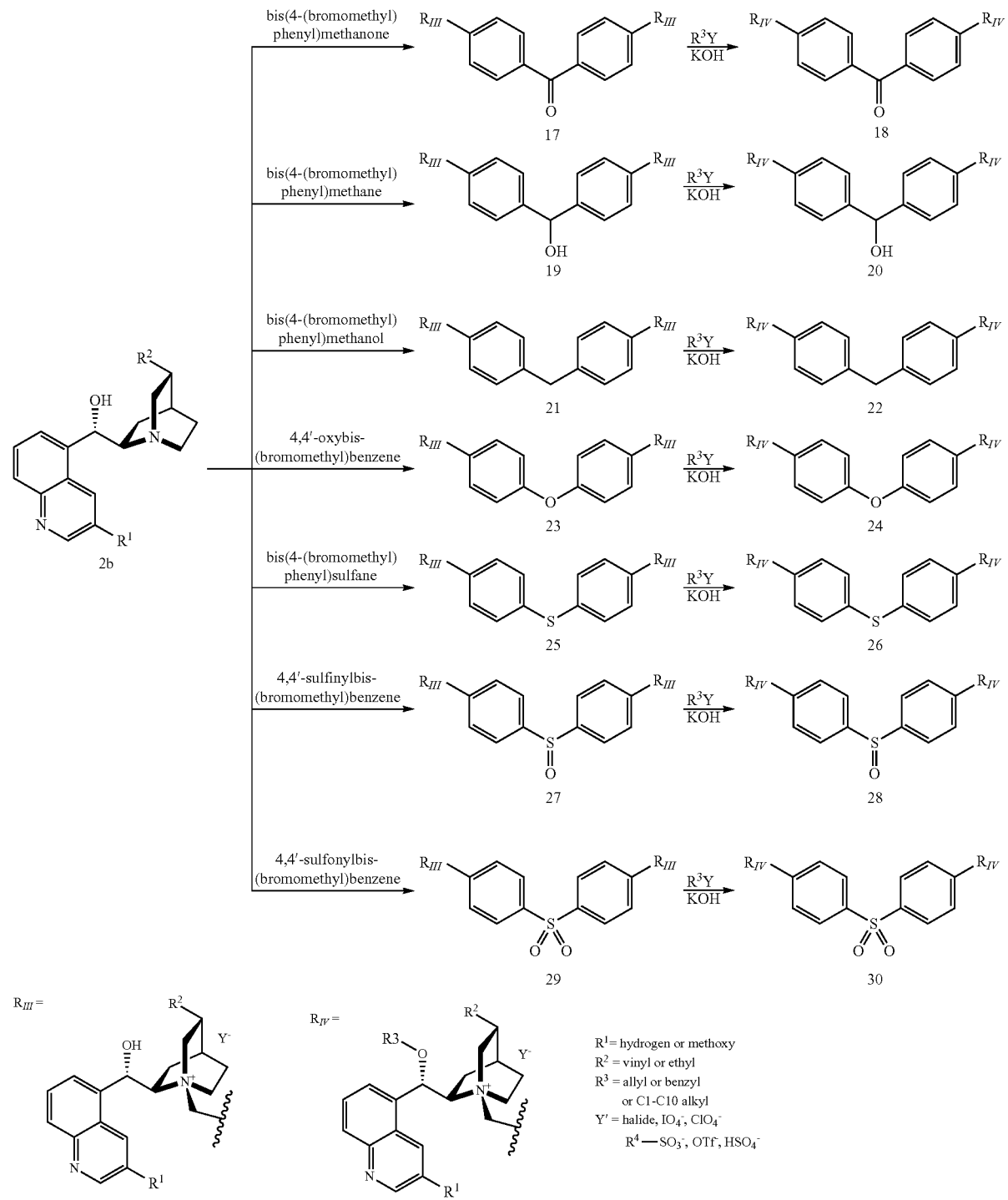

[Reaction Scheme 3]

In one experimental example of the present invention, as a result of synthesizing asymmetric alpha-amino acids using the cinchona alkaloid compounds represented by the Formulas 3 to 30 prepared according to the synthesis strategies of Reaction Schemes 2 and 3 as a chiral phase-transfer catalyst, the reaction is performed under improved reaction conditions compared with the conventional method, and an optical purity is also remarkably improved compared with a conventional mono-benzyl ammonium catalyst. Therefore, it is confirmed that the novel cinchona alkaloid compound of the present invention can be applied as the core technology for the fields of synthesis and production of alpha-amino acids.

Accordingly, the present invention provides a method of synthesizing an alpha-amino acid using the cinchona alkaloid compound of Formula 1 as a chiral phase-transfer catalyst, a composition including the cinchona alkaloid compound as an active ingredient for synthesizing an alpha-amino acid, and the use of the cinchona alkaloid compound for synthesizing an alpha-amino acid.

Meanwhile, the method of synthesizing an alpha-amino acid using the cinchona alkaloid compound of the present invention as a catalyst may exhibit high optical purity even at room temperature, a low catalytic amount and an almost equivalent of a reagent, and thus industrial application is simple. In addition, unlike a benzene ring or naphthyl ring used as a linker in a conventional dimeric catalyst, the dimeric ammonium catalyst of the present invention connected through the linker —X— may have elasticity and rotatability as a curved shape, may be adjusted in a more suitable structure for a corresponding catalytic reaction and thereby exhibit better catalytic efficiency, and similar elasticity and rotatability may also be expected through the combination of —XX— or —X—X'—. Therefore, more improved catalytic functions may be expected.

In one exemplary embodiment, as shown in Reaction Scheme 1, a method of synthesizing an alpha-amino acid includes preparing a compound of Formula III by reacting a compound of Formula I with a compound of Formula II in the presence of the cinchona alkaloid compound, which is a chiral phase-transfer catalyst, and preparing a compound of Formula IV by hydrolyzing the compound of Formula III prepared in the above step under an acidic condition. However, this method is merely an example of the method of preparing an alpha-amino acid, which may include any method of synthesizing an amino acid with specific chirality without limitation.

[Reaction Scheme 1]

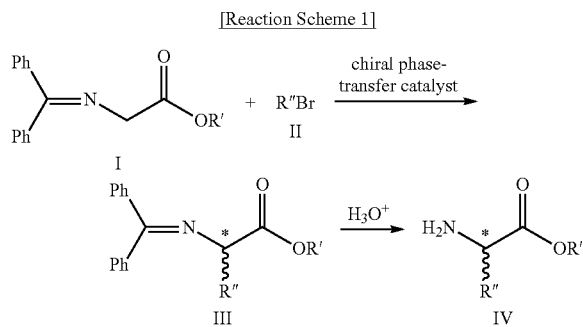

Meanwhile, in Reaction Scheme 1, R' may be $C_2$-$C_6$ alkyl, R" may be $C_2$-$C_6$ alkyl or $C_5$-$C_{10}$ aryl, and preferably, R' is tert-butyl, alkyl and R" is benzyl, but the present invention is not limited thereto.

In addition, the step of reacting the compound of Formula I with the compound of Formula II is preferably performed at 10 to 20° C., more preferably at 13 to 17° C., and most preferably at 15° C. The compound of Formula II is preferably used at 0.8 to 1.6 equivalents, more preferably at 1.0 to 1.4 equivalents, and most preferably at 1.2 equivalents per equivalent of the compound of Formula I. The chiral phase-transfer catalyst is preferably used at an amount ranging from 0.008 to 0.012 equivalents (0.05 to 1.2% equivalent), more preferably 0.009 to 0.011 equivalents (0.9 to 1.1% equivalent), and most preferably 0.010 equivalents (1.0% equivalent), but the present invention is not limited thereto.

Hereinafter, to aid in understanding the present invention, exemplary examples will be suggested. However, the following examples are merely provided to more easily understand the present invention and not to limit the present invention.

Example 1.
4,4'-bis(cinchonidium-N-methyl)biphenyl Methanone Dibromide (3)

To a 25-mL round bottom flask, (−)-cinchonidine (145 mg, 0.49 mmol) and bis(4-(bromomethyl) phenyl) methanone (100 mg, 0.27 mmol) were added, and refluxed with stirring at 110° C. for 4 hours in a toluene solvent (5 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (205 mg) as a desired product.
$^1$H NMR (300 MHz, DMSO-$d_6$) δ 9.00 (d, J=4.5 Hz, 2H), 8.35 (d, J=8.4 Hz, 2H), 8.12 (dd, J=8.3, 1.6 Hz, 2H), 7.99 (m, 8H), 7.94-7.71 (m, 6H), 6.82 (m, 2H), 6.60 (m, 2H), 5.80-5.62 (m, 2H), 5.35 (m, 2H), 5.20 (d, J=17.3 Hz, 4H), 4.98 (d, J=10.6 Hz, 2H), 4.38 (m, 2H), 4.15-3.94 (m, 2H), 3.87 (m, 2H), 3.41 (m, 2H), 3.17 (m, 2H), 2.72 (m, 2H), 2.13 (m, 4H), 2.03 (m, 2H), 1.85 (m, 2H), 1.40-1.21 (m, 2H).

Example 2. 4,4'-bis(O(9)-allylcinchonidium-N-methyl)biphenyl Methanone Dibromide After Compound 3 (304 mg, 0.31 mmol) obtained by the method of Example 1 was suspended in dichloromethane (10 mL), a 50% potassium hydroxide solution (0.35 mL, 3.1 mmol) and allyl bromide (0.16 mL, 1.9 mmol) were added, and then the mixture was stirred at room temperature for 2 hours. The reaction mixture was diluted with water (5 mL), and an organic layer was separated. A dichloromethane solution was dried over anhydrous magnesium sulfate and filtered. The resulting filtrate was added dropwise to ethyl ether (50 mL), thereby obtaining a solid. The resulting solid was separated and purified by column chromatography (dichloromethane/methanol) to obtain a pale orange solid (270 mg) as a desired product.
$^1$H NMR (300 MHz, Chloroform-d) δ 8.98 (m, 2H), 8.81 (d, J=8.5 Hz, 2H), 8.20-8.10 (m, 6H), 7.86 (m, 4H), 7.83-7.69 (m, 6H), 6.73 (d, J=11.5 Hz, 2H), 6.24 (m, 2H), 6.27-6.04 (m, 2H), 5.64-5.52 (m, 2H), 5.42 (m, 6H), 5.02 (m, 4H), 4.77 (d, J=10.7 Hz, 2H), 4.64 (m, 2H), 4.29 (m, 4H), 4.13 (m, 2H), 3.58 (m, 2H), 3.44 (m, 2H), 2.71 (m, 2H), 2.12 (m, 4H), 1.99 (m, 4H), 1.41 (m, 2H).

Example 3.
4,4'-bis(hydrocinchonidium-N-methyl)biphenyl Methanone Dibromide (3-1)

To a 25-mL round bottom flask, (−)-hydrocinchonidine (292 mg, 0.98 mmol) and bis(4-(bromomethyl)phenyl)

methanone (200 mg, 0.55 mmol) were added, and refluxed with stirring at 110° C. for 3 hours in a mixed solvent of ethanol:N,N-dimethylformamide:chloroform (5:6:2) (3 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (300 mg) as a desired product.

$^1$H NMR (300 MHz, DMSO-$d_6$) δ 9.01 (d, J=4.4 Hz, 2H), 8.36 (d, J=8.6 Hz, 2H), 8.12 (d, J=8.3 Hz, 2H), 8.05 (m, 6H), 7.82 (m, 4H), 7.71 (m, 4H), 6.79 (m, 2H), 6.60 (m, 2H), 5.39 (d, J=12.2 Hz, 2H), 5.14 (d, J=12.3 Hz, 2H), 4.43-4.36 (m, 2H), 4.06-3.95 (m, 2H), 3.58 (m, 2H), 3.42-3.20 (m, 4H), 2.10 (m, 4H), 2.00 (m, 2H), 1.77 (m, 4H), 1.35 (m, 2H), 1.20 (m, 4H), 0.73 (m, 6H).

Example 4. 4,4'-bis(O(9)-allylhydrocinchonidium-N-methyl)biphenyl Methanone Dibromide (4-1)

After Compound 3-1 (200 mg, 0.21 mmol) obtained by the method of Example 3 was suspended in dichloromethane (3 mL), a 50% potassium hydroxide solution (0.25 mL, 2.2 mmol) and allyl bromide (0.127 mL, 1.46 mmol) were added, and then the mixture was stirred at room temperature for 3 hours. The reaction mixture was diluted with water (5 mL), and an organic layer was separated. A dichloromethane solution was dried over anhydrous magnesium sulfate and filtered. The resulting solution was distilled under reduced pressure, thereby obtaining a solid. The resulting solid was separated and purified by column chromatography (dichloromethane/methanol) to obtain a pale orange solid (144 mg) as a desired product.

$^1$H NMR (300 MHz, Chloroform-d) δ 8.99 (d, J=4.5 Hz, 2H), 8.83 (d, J=8.6 Hz, 2H), 8.14 (m, 4H), 8.12 (m, 2H), 7.82 (m, 2H), 7.79 (m, 4H), 7.75 (m, 4H), 6.51 (d, J=11.9 Hz, 2H), 6.31 (m, 2H), 6.14 (m, 2H), 5.50 (m, 2H), 5.36 (m, 2H), 4.81 (d, J=11.9 Hz, 2H), 4.70 (m, 4H), 4.41 (m, 2H), 4.33 (m, 2H), 4.08 (m, 2H), 3.46 (m, 2H), 3.32 (m, 2H), 2.27 (m, 4H), 2.11 (m, 2H), 2.05 (m, 4H), 1.47 (m, 4H), 1.33-1.19 (m, 2H), 0.78 (m, 6H).

Example 5.
3,4'-bis(cinchonidium-N-methyl)biphenyl Methanone Dibromide (3-2)

In a 25-mL round bottom flask, (3-(bromomethyl)phenyl)(4-(bromomethyl)phenyl)methanone (300 mg, 0.815 mmol) was added to (–)-cinchonidine (432 mg, 1.46 mmol), and refluxed with stirring at 110° C. for 5 hours in a mixed solvent of ethanol:N,N-dimethylformamide:chloroform (5:6:2) (4 mL). The reaction mixture was cooled to room temperature and added dropwise to ether (200 mL) to precipitate a solid, followed by filtering under reduced pressure. The obtained solid was separated and purified by column chromatography (dichloromethane/methanol) to obtain a white solid (238 mg) as a desired product.

$^1$H NMR (300 MHz, DMSO-$d_6$) δ 8.98 (m, 2H), 8.41-8.28 (m, 3H), 8.06 (m, 4H), 7.94 (s, 4H), 7.89-7.69 (m, 7H), 6.85-6.72 (m, 2H), 6.57 (m, 2H), 5.72-5.55 (m, 2H), 5.39-5.01 (m, 6H), 4.9-4.74 (m, 2H), 4.34 (m, 2H), 3.98 (m, 2H), 3.83 (m, 2H), 3.62 (m, 2H), 3.40-3.21 (m, 2H), 2.73 (m, 2H), 2.18-1.81 (m, 8H), 1.23 (m, 2H).

Example 6. 3,4'-bis(O(9)-allylcinchonidium-N-methyl)biphenyl Methanone Dibromide (4-2)

After Compound 3-2 (200 mg, 0.209 mmol) obtained by the method of Example 5 was suspended in dichloromethane (4 mL), a 50% potassium hydroxide solution (0.25 mL, 2.2 mmol) and allyl bromide (178 mg, 1.46 mmol) were added, and then the mixture was stirred at room temperature for 4.5 hours. The reaction mixture was diluted with water (5 mL), and an organic layer was separated. A dichloromethane solution was dried over anhydrous magnesium sulfate and filtered. The resulting solid was separated and purified by column chromatography (dichloromethane/methanol) to obtain a pale yellow solid (162 mg) as a desired product.

$^1$H NMR (300 MHz, Chloroform-d) δ 9.06-8.87 (m, 1H), 8.86-8.70 (m, 1H), 8.14 (d, J=8.8 Hz, 2H), 7.94-7.55 (m, 2H), 6.59 (t, J=12.4 Hz, 2H), 6.35-5.97 (m, 4H), 5.70-5.49 (m, 2H), 5.48-5.34 (m, 6H), 5.01-4.78 (m, 4H), 4.33-4.20 (m, 4H), 4.08-3.96 (m, 2H), 3.72 (m, 1H), 3.43 (m, 1H), 3.08 (m, 1H), 2.91 (m, 1H), 2.71-2.43 (m, 2H), 2.27-1.96 (m, 4H), 1.89 (m, 4H), 1.39 (m, 2H).

Example 7.
3,3'-bis(cinchonidium-N-methyl)biphenyl Methanone Dibromide (3-3)

In a 25-mL round bottom flask, bis(3-(bromomethyl)phenyl)methanone (300 mg, 0.815 mmol) was added to (–)-cinchonidine (456 mg, 1.55 mmol), and refluxed with stirring at 110° C. for 6.5 hours in a mixed solvent of ethanol:N,N-dimethylformamide:chloroform (5:6:2) (4.5 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale yellow solid (225 mg) as a desired product.

$^1$H NMR (300 MHz, DMSO-$d_6$) δ 8.98 (d, J=4.5 Hz, 2H), 8.34 (d, J=8.7 Hz, 2H), 8.27 (s, 2H), 8.08 (d, J=8.3 Hz, 4H), 7.97 (d, J=7.7 Hz, 2H), 7.86-7.69 (m, 8H), 6.74 (d, J=5.0 Hz, 2H), 6.56 (m, 2H), 5.70-5.59 (m, 2H), 5.41 (d, J=14.5 Hz, 2H), 5.27 (m, 4H), 4.94 (d, J=10.5 Hz, 2H), 4.34 (m, 2H), 3.97-3.89 (m, 4H), 3.49 (m, 2H), 3.30 (m, 2H), 2.74 (m, 2H), 2.09 (m, 4H), 1.99 (m, 2H), 1.87 (m, 2H), 1.28 (m, 2H).

Example 8. 3,3'-bis(O(9)-allylcinchonidium-N-methyl)biphenyl Methanone Dibromide (4-3)

After Compound 3-3 (100 mg, 0.105 mmol) obtained by the method of Example 7 was suspended in dichloromethane (1.7 mL), a 50% potassium hydroxide solution (0.15 mL, 4.06 mmol) and allyl bromide (88.50 mg, 0.732 mmol) were added, and then the mixture was stirred at room temperature for 2.5 hours. The reaction mixture was diluted with water (5 mL), and an organic layer was separated. A dichloromethane solution was dried over anhydrous magnesium sulfate and filtered. The resulting solid was separated and purified by column chromatography (dichloromethane/methanol) to obtain a pale yellow solid (83 mg) as a desired product.

$^1$H NMR (300 MHz, Chloroform-d) δ 8.96 (d, J=4.5 Hz, 2H), 8.81 (d, J=8.5 Hz, 2H), 8.50 (m, 2H), 8.12 (m, 4H), 7.84 (m, 4H), 7.74 (m, 2H), 7.69-7.52 (m, 4H), 6.47 (d, J=12.1 Hz, 2H), 6.32 (m, 2H), 6.22-6.05 (m, 2H), 5.62 (m, 2H), 5.46-5.39 (m, 2H), 5.39-5.32 (m, 3H), 5.29 (m, 1H), 4.98-4.90 (m, 2H), 4.86 (m, 2H), 4.64 (d, J=11.9 Hz, 2H), 4.52 (m, 2H), 4.42-4.28 (m, 2H), 4.23 (m, J=5.6 Hz, 4H), 3.65 (d, J=7.3 Hz, 2H), 3.58-3.43 (m, 2H), 2.81 (m, 2H), 2.22-2.03 (m, 8H), 1.50-1.36 (m, 2H).

Example 9.
4,4'-bis(cinchonidium-N-methyl)biphenyl Methane Dibromide (5)

To a 25-mL round bottom flask, bis(4-(bromomethyl)phenyl)methane (300 mg, 0.847 mmol) was added to (–)- cinchonidine (449 mg, 1.52 mmol), and refluxed with stirring at 110° C. for 3.5 hours in a mixed solvent of ethanol:N,N-dimethylformamide:chloroform (5:6:2) (4 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (352 mg) as a desired product.

$^1$H NMR (300 MHz, DMSO-$d_6$) δ 8.98 (d, J=4.4 Hz, 2H), 8.31 (d, J=8.5 Hz, 2H), 8.10 (dd, J=8.4, 1.3 Hz, 2H), 7.88-7.65 (m, 10H), 7.49 (d, J=8.1 Hz, 4H), 6.73 (d, J=4.9 Hz, 2H), 6.55 (d, J=4.9 Hz, 2H), 5.73-5.58 (m, 2H), 5.27-5.10 (m, 4H), 5.06 (d, J=12.2 Hz, 2H), 4.95 (d, J=10.5 Hz, 2H), 4.40-4.21 (m, 2H), 4.14 (s, 2H), 4.09-3.86 (m, 4H), 3.85-3.72 (m, 2H), 3.40-3.30 (m, 2H), 2.69 (d, J=7.9 Hz, 2H), 2.16-1.94 (m, 6H), 1.91-1.74 (m, 2H), 1.37-1.20 (m, 2H).

Example 10. 4,4'-bis(O(9)-allylcinchonidium-N-methyl)biphenyl Methane Dibromide (6)

After Compound 5 (280 mg, 0.297 mmol) obtained by the method of Example 9 was suspended in dichloromethane (7 mL), a 50% potassium hydroxide solution (0.35 mL, 3.1 mmol) and allyl bromide (254 mg, 2.08 mmol) were added, and then the mixture was stirred at room temperature for 2.5 hours. The reaction mixture was diluted with water (5 mL), and an organic layer was separated. A dichloromethane solution was dried over anhydrous magnesium sulfate and filtered. The resulting filtrate was distilled under reduced pressure to obtain a solid. The resulting solid was separated and purified by column chromatography (dichloromethane/methanol) to obtain a pale yellow solid (141.6 mg) as a desired product.

$^1$H NMR (300 MHz, Chloroform-d) δ 8.98 (d, J=4.5 Hz, 2H), 8.82 (d, J=8.5 Hz, 2H), 8.14 (d, J=8.4 Hz, 2H), 8.02-7.41 (m, 10H), 7.34-7.23 (m, 4H), 6.47 (d, J=11.8 Hz, 2H), 6.22 (m, 2H), 6.11 (m, 2H), 5.68 (m, 2H), 5.38 (m, 6H), 4.98 (m, 2H), 4.82 (d, J=14.1 Hz, 2H), 4.65 (d, J=12.1 Hz, 4H), 4.29 (m, 4H), 4.08 (s, 2H), 4.03 (m, 2H), 3.44 (m, 6.9 Hz, 2H), 3.26 (m, 2H), 2.68 (m, 2H), 2.16-2.07 (m, 6H), 1.92 (m, 2H), 1.40 (m, 2H).

Example 11. 4,4'-bis(hydrocinchonidium-N-methyl)biphenyl Methane Dibromide (5-1)

To a 25-mL round bottom flask, bis(4-(bromomethyl)phenyl)methane (300 mg, 0.847 mmol) was added to (−)-hydrocinchonidine (452 mg, 1.52 mmol), and refluxed with stirring at 110° C. for 3.5 hours in a mixed solvent of ethanol:N,N-dimethylformamide:chloroform (5:6:2) (5 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (495.7 mg) as a desired product.

$^1$H NMR (300 MHz, DMSO-$d_6$) δ 8.98 (d, J=4.5 Hz, 2H), 8.29 (d, J=8.5 Hz, 2H), 8.10 (d, J=8.3 Hz, 2H), 7.89-7.76 (m, 4H), 7.75-7.57 (m, 6H), 7.48 (d, J=8.1 Hz, 4H), 6.71 (m, 2H), 6.55 (m, 2H), 5.22 (d, J=12.4 Hz, 2H), 4.94 (d, J=12.3 Hz, 2H), 4.31 (m, 2H), 4.13 (s, 2H), 3.95 (m, 2H), 3.52-3.41 (m, 2H), 3.20-3.13 (m, 2H), 3.04 (t, J=7.3 Hz, 2H), 2.14-2.00 (m, 4H), 1.97-1.88 (m, 2H), 1.84-1.67 (m, 4H), 1.42-1.28 (m, 2H), 1.17 (m, 4H), 0.69 (m, 6H).

Example 12. 4,4'-bis(O(9)-allylhydrocinchonidium-N-methyl)biphenyl Methane Dibromide (6-1)

After Compound 5-1 (300 mg, 0.317 mmol) obtained by the method of Example 11 was suspended in dichloromethane (7 mL), a 50% potassium hydroxide solution (0.35 mL, 3.1 mmol) and allyl bromide (271 mg, 2.22 mmol) were added, and then the mixture was stirred at room temperature for 3 hours. The reaction mixture was diluted with water (5 mL), and an organic layer was separated. A dichloromethane solution was dried over anhydrous magnesium sulfate and filtered. The resulting solid was separated and purified by column chromatography (dichloromethane/methanol) to obtain a pale yellow solid (228 mg) as a desired product.

$^1$H NMR (300 MHz, Chloroform-d) δ 8.97 (d, J=4.5 Hz, 2H), 8.80 (d, J=8.5 Hz, 2H), 8.13 (d, J=8.4 Hz, 2H), 7.94-7.66 (m, 10H), 7.31 (d, J=5.2 Hz, 4H), 6.33-6.19 (m, 4H), 6.10 (m, 2H), 5.40 (d, J=6.5 Hz, 2H), 4.70 (d, J=11.9 Hz, 4H), 4.61-4.50 (m, 2H), 4.33-4.18 (m, 4H), 4.11 (d, J=6.7 Hz, 2H), 4.06 (s, 2H), 3.37 (m, 2H), 3.31-3.19 (m, 2H), 2.17 (m, 4H), 2.03 (m, 2H), 1.84 (m, 4H), 1.44 (m, 4H), 1.25-1.15 (m, 2H), 0.76 (t, J=7.3 Hz, 6H).

Example 13. 4,4'-bis(quinium-N-methyl)biphenyl Methane Dibromide (5-2)

To a 25-mL round bottom flask, bis(4-(bromomethyl)phenyl)methane (200 mg, 0.565 mmol) was added to (−)-quinine (330 mg, 1.02 mmol), and refluxed with stirring at 110° C. for 4 hours in a mixed solvent of ethanol:N,N-dimethylformamide:chloroform (5:6:2) (3 mL). The reaction mixture was cooled to room temperature and added dropwise to ether (200 mL) to precipitate a solid, followed by filtering under reduced pressure. The obtained solid was separated and purified by column chromatography (dichloromethane/methanol) to obtain a pale yellow solid (301 mg) as a desired product.

$^1$H NMR (300 MHz, DMSO-$d_6$) δ 8.81 (d, J=4.5 Hz, 2H), 8.02 (dd, J=9.2, 2.8 Hz, 2H), 7.75 (d, J=4.5 Hz, 2H), 7.68 (d, J=8.2 Hz, 4H), 7.48 (dd, J=7.1, 2.4 Hz, 6H), 7.42 (d, J=2.7 Hz, 2H), 6.70-6.55 (m, 4H), 5.75 (dddd, J=17.2, 9.5, 6.8, 2.7 Hz, 2H), 5.47 (d, J=12.3 Hz, 2H), 5.13 (m, 2H), 5.01 (m, 2H), 4.74 (d, J=12.2 Hz, 2H), 4.39-4.24 (m, 2H), 4.12 (s, 2H), 4.02 (s, 6H), 3.90 (t, J=8.8 Hz, 2H), 3.79-3.62 (m, 2H), 3.44-3.31 (m, 2H), 3.24 (m, 2H), 2.79-2.64 (m, 2H), 2.32-2.10 (m, 4H), 2.06-1.97 (m, 2H), 1.93-1.78 (m, 2H), 1.56-1.41 (m, 2H).

Example 14. 4,4'-bis(O(9)-allylquinium-N-methyl)biphenyl Methane Dibromide (6-2)

After Compound 5-2 (150 mg, 0.150 mmol) obtained by the method of Example 13 was suspended in dichloromethane (3 mL), a 50% potassium hydroxide solution (0.35 mL, 3.1 mmol) and allyl bromide (0.128 mg, 1.05 mmol) were added, and then the mixture was stirred at room temperature for 3 hours. The reaction mixture was diluted with water (5 mL), and an organic layer was separated. A dichloromethane solution was dried over anhydrous magnesium sulfate and filtered. The obtained solid was purified by column chromatography (dichloromethane/methanol) to obtain a pale yellow solid (107 mg) as a desired product.

$^1$H NMR (300 MHz, DMSO-$d_6$) δ 8.83 (d, J=4.5 Hz, 2H), 8.04 (d, J=9.1 Hz, 2H), 7.73-7.61 (m, 6H), 7.55-7.40 (m,

8H), 6.57 (m, 2H), 6.24-6.05 (m, 2H), 5.81-5.67 (m, 2H), 5.59 (d, J=12.4 Hz, 2H), 5.46 (m, 2H), 5.28 (dd, J=10.5, 1.6 Hz, 2H), 5.15-4.97 (m, 4H), 4.75 (d, J=12.2 Hz, 2H), 4.50 (dd, J=12.6, 5.3 Hz, 2H), 4.13 (s, 2H), 4.00 (m, 8H), 3.98-3.89 (m, 4H), 3.38-3.29 (m, 4H), 2.78-2.63 (m, 2H), 2.44-2.32 (m, 2H), 2.24-2.12 (m, 2H), 2.07-2.00 (m, 2H), 1.96-1.83 (m, 2H), 1.61-1.49 (m, 2H), 1.23 (m, 2H).

Example 15.
4,4'-bis(cinchonidium-N-methyl)biphenyl Methanol Dibromide (7)

To a 25-mL round bottom flask, bis(4-(bromomethyl)phenyl)methanol (100 mg, 0.27 mmol) was added to (−)-cinchonidine (151 mg, 0.513 mmol), and refluxed with stirring at 110° C. for 1 hour in a mixed solvent of ethanol:N,N-dimethylformamide:chloroform (5:6:2) (1.5 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale yellow solid (70 mg) as a desired product.

$^1$H NMR (300 MHz, DMSO-$d_6$) δ 8.98 (d, J=4.5 Hz, 2H), 8.29 (d, J=8.2 Hz, 2H), 8.10 (m, 2H), 7.89-7.78 (m, 5H), 7.74 (m, 5H), 7.64 (d, J=8.4 Hz, 4H), 6.79 (d, J=4.7 Hz, 2H), 6.55 (d, J=4.7 Hz, 2H), 6.23 (d, J=4.4 Hz, 1H), 5.90 (d, J=4.5 Hz, 1H), 5.67 (m, 2H), 5.28-5.12 (m, 4H), 5.03 (d, J=12.2 Hz, 2H), 4.95 (d, J=10.5 Hz, 2H), 4.30 (m, 2H), 4.03-3.86 (m, 2H), 3.79 (d, J=9.9 Hz, 2H), 3.35-3.12 (m, 4H), 2.70 (m, 2H), 2.16-1.91 (m, 6H), 1.82 (m, 2H), 1.33-1.21 (m, 2H).

Example 16. 4,4'-bis(O(9)-allylcinchonidium-N-methyl)biphenyl Methanol Dibromide (8)

Compound 7 (70 mg, 0.073 mmol) obtained by the method of Example 15 was suspended in dichloromethane (1.4 mL), a 50% potassium hydroxide solution (0.11 mL, 3.0 mmol) and allyl bromide (88 mg, 0.73 mmol) were added, and then the mixture was stirred at room temperature for 2 hours. The reaction mixture was diluted with water (5 mL), and an organic layer was separated. A dichloromethane solution was dried over anhydrous magnesium sulfate and filtered. The obtained solid was purified by column chromatography (dichloromethane/methanol) to obtain a pale yellow solid (25 mg) as a desired product.

$^1$H NMR (300 MHz, Chloroform-d) δ 8.98 (d, J=4.5 Hz, 2H), 8.83 (d, J=8.6 Hz, 2H), 8.14 (m, 2H), 7.96 (d, J=7.4 Hz, 4H), 7.78 (m, 4H), 7.62 (d, J=7.5 Hz, 2H), 7.57-7.39 (m, 4H), 6.51 (d, J=11.9 Hz, 2H), 6.25 (m, 2H), 6.20-6.04 (m, 2H), 6.04-5.90 (m, 1H), 5.66 (m, 2H), 5.55 (s, 1H), 5.44-5.35 (m, 4H), 5.06-4.93 (m, 2H), 4.83 (d, J=10.9 Hz, 2H), 4.76-4.47 (m, 4H), 4.24 (m, 4H), 4.13-3.92 (m, 4H), 3.43 (m, 2H), 3.33-3.16 (m, 2H), 2.68 (m, 2H), 2.11 (d, J=13.8 Hz, 8H), 1.91 (d, J=5.7 Hz, 2H), 1.40 (d, J=11.7 Hz, 2H), 1.28 (d, J=15.9 Hz, 2H).

Example 17.
4,4'-bis(hydrocinchonidium-N-methyl)biphenyl Methanol Dibromide (7-1)

To a 25-mL round bottom flask, bis(4-(bromomethyl)phenyl)methanol (100 mg, 0.2702 mmol) was added to (−)-hydrocinchonidine (152.2 mg, 0.5134 mmol), and refluxed with stirring at 110° C. for 1.5 hours in a mixed solvent of ethanol:N,N-dimethylformamide:chloroform (5:6:2) (1.5 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale orange solid (130 mg) as a desired product.

$^1$H NMR (300 MHz, DMSO-$d_6$) δ 8.98 (m, 2H), 8.26 (m, 2H), 8.11 (d, J=8.4 Hz, 2H), 7.90-7.79 (m, 4H), 7.77-7.56 (m, 10H), 6.73 (m, 2H), 6.53 (m, 2H), 6.26-6.16 (m, 1H), 5.91-5.84 (m, 1H), 5.24-5.03 (m, 2H), 4.89 (m, 2H), 4.63-4.37 (m, 2H), 4.27 (d, J=10.9 Hz, 2H), 4.08-3.76 (m, 4H), 3.22 (d, J=10.7 Hz, 4H), 2.18-1.87 (m, 8H), 1.76 (m, 6H), 1.32 (m, 2H), 1.16 (m, 4H).

Example 18. 4,4'-bis(O(9)-allylhydrocinchonidium-N-methyl)biphenyl Methanol Dibromide (8-1)

After Compound 7-1 (90 mg, 0.0935 mmol) obtained by the method of Example 17 was suspended in dichloromethane (1.6 mL), a 50% potassium hydroxide solution (0.14 mL, 3.79 mmol) and allyl bromide (118.7 mg, 0.9813 mmol) were added, and then the mixture was stirred at room temperature for 2.5 hours. The reaction mixture was diluted with water (5 mL), and an organic layer was separated. A dichloromethane solution was dried over anhydrous magnesium sulfate and filtered. The obtained solid was separated and purified by column chromatography (methylene chloride/methanol) to obtain a pale yellow solid (87 mg) as a desired product.

$^1$H NMR (300 MHz, DMSO-$d_6$) δ 8.98 (m, 2H), 8.82 (d, J=8.5 Hz, 2H), 8.19-8.11 (m, 2H), 7.98-7.75 (m, 8H), 7.62-7.53 (m, 2H), 7.49 (m, 4H), 6.28 (m, 4H), 6.08-5.89 (m, 3H), 5.55 (m, 1H), 5.43-5.34 (m, 4H), 5.21-5.09 (m, 2H), 4.61 (m, 4H), 4.27 (m, 4H), 4.08-3.92 (m, 6H), 3.38 (d, J=14.7 Hz, 2H), 3.22 (m, 2H), 2.14 (m, 4H), 2.04 (m, 6H), 1.39 (m, 4H), 1.23 (m, 2H), 0.77 (m, 6H).

Example 19.
4,4'-bis(cinchonidium-N-methyl)biphenyl Ether Dibromide (9)

To a 25-mL round bottom flask, 4,4'-oxybis(bromomethyl)benzene (200 mg, 0.56 mmol) was added to (−)-cinchonidine (314 mg, 1.07 mmol), and refluxed with stirring at 110° C. for 4 hours in a mixed solvent of ethanol:N,N-dimethylformamide:chloroform (5:6:2) (3 mL). The reaction mixture was cooled to room temperature and added dropwise to ether (50 mL) to precipitate a solid, followed by filtering under reduced pressure. The obtained solid was recrystallized with methanol-ether to obtain a pale yellow solid (283 mg) as a desired product.

$^1$H NMR (300 MHz, DMSO-$d_6$) δ 8.98 (d, J=4.5 Hz, 2H), 8.39-8.28 (d, 2H), 8.11 (d, J=8.3, 1.4 Hz, 2H), 7.92-7.70 (m, 10H), 7.28 (d, J=8.2 Hz, 4H), 6.74 (d, J=4.8 Hz, 2H), 6.66-6.51 (m, 2H), 5.79-5.59 (m, 2H), 5.27 (d, J=12.4 Hz, 2H), 5.19 (d, J=17.2, 1.3 Hz, 2H), 5.11 (d, J=12.2 Hz, 2H), 4.96 (d, J=10.5, 1.4 Hz, 2H), 4.32 (m, 2H), 3.97 (t, J=9.2 Hz, 2H), 3.81 (m, 2H), 3.41 (t, J=11.6 Hz, 2H), 3.25 (m, 2H), 2.11 (m, 6H), 1.86 (m, 2H), 1.32 (m, 2H).

Example 19-1.
3,3'-bis(cinchonidium-N-methyl)biphenyl Ether Dibromide (9-1)

To a 25-mL round bottom flask, 3,3'-oxybis(bromomethyl)benzene (150 mg, 0.421 mmol) was added to (−)-cinchonidine (223.2 mg, 0.758 mmol), and refluxed with stirring for 5 hours in a mixed solvent of ethanol:N,N- dimethylformamide:chloroform (5:6:2) (3 mL). The reaction mixture was cooled to room temperature and added dropwise to ether (100 mL) to precipitate a solid, followed by filtering under reduced pressure. The obtained solid was recrystallized with methanol-ether to obtain a light brown solid (227 mg) as a desired product.

$^1$H NMR (300 MHz, DMSO-$d_6$) δ 9.00-8.94 (m, 2H), 8.31 (d, J=7.6 Hz, 2H), 8.08 (m, 2H), 7.87-7.77 (m, 4H), 7.73 (m, 2H), 7.69-7.64 (m, 2H), 7.58 (m, 4H), 7.32 (m, 2H), 6.72 (d, J=5.0 Hz, 2H), 6.51 (m, 2H), 5.66 (m, 2H), 5.35-5.08 (m, 6H), 4.99-4.88 (m, 2H), 4.30 (s, 2H), 3.94 (t, J=8.6 Hz, 2H), 3.85 (m, 2H), 3.58-3.45 (m, 2H), 3.34 (d, J=4.9 Hz, 2H), 2.79 (m, 2H), 2.17-1.82 (m, 8H), 1.24 (m, 2H).

Example 20. 4,4'-bis(O(9)-allylcinchonidium-N-methyl)biphenyl Ether Dibromide (10)

After Compound 9 (180 mg, 0.190 mmol) obtained by the method of Example 19 was suspended in dichloromethane (3 mL), a 50% potassium hydroxide solution (0.25 mL, 2.2 mmol) and allyl bromide (0.11 mL, 1.33 mmol) were added, and then the mixture was stirred at room temperature for 4 hours. The reaction mixture was diluted with water (3 mL), and an organic layer was separated. A dichloromethane solution was dried over anhydrous magnesium sulfate and filtered. The resulting filtrate was added dropwise to ethyl ether (50 mL), thereby obtaining a solid. The obtained solid was separated and purified by column chromatography (dichloromethane/methanol) to obtain a pale orange solid (200 mg) as a desired product.

$^1$H NMR (300 MHz, Chloroform-d) δ 8.99 (d, J=4.4 Hz, 2H), 8.86 (d, J=8.5 Hz, 2H), 8.15 (d, J=8.3 Hz, 2H), 8.02 (d, J=8.3 Hz, 4H), 7.88 (m, 2H), 7.77 (m, 2H), 7.63 (s, 2H), 7.19-7.03 (m, 4H), 6.56 (d, J=11.7 Hz, 2H), 6.23 (m, 2H), 6.19-6.07 (m, 2H), 5.67 (m, 2H), 5.49-5.32 (m, 6H), 4.98 (d, J=10.4 Hz, 2H), 4.89 (m, 2H), 4.64 (m, 4H), 4.29 (m, 4H), 4.07 (m, 2H), 3.52 (m, 2H), 3.33 (m, 2H), 2.73 (m, 2H), 2.15-1.96 (m, 8H), 1.42 (m, 2H).

Example 20-1: 3,3'-bis(O(9)-allylcinchonidium-N-methyl)biphenyl Ether Dibromide (10-1)

After Compound 9-1 (70 mg, 0.074 mmol) obtained by the method of Example 19-1 was suspended in dichloromethane (2 mL), a 50% potassium hydroxide solution (0.25 mL, 6.77 mmol) and allyl bromide (0.043 mL, 0.518 mmol) were added, and then the mixture was stirred in iced water for 4 hours. The reaction mixture was diluted with water (2 mL), and an organic layer was separated. A dichloromethane solution was dried over anhydrous magnesium sulfate and filtered. The resulting filtrate was added dropwise to ethyl ether (50 mL), thereby obtaining a solid. The obtained solid was separated and purified by column chromatography (dichloromethane/methanol) to obtain a pale yellow solid (60.0 mg) as a desired product.

$^1$H NMR (300 MHz, Chloroform-d) δ 8.95 (d, J=4.5 Hz, 2H), 8.77 (d, J=8.8 Hz, 2H), 8.12 (m, 2H), 8.04 (m, 2H), 7.87 (m, 2H), 7.75 (m, 2H), 7.65 (m, 2H), 7.48 (m, 2H), 7.35 (m, 2H), 7.18 (m, 2H), 6.35 (d, J=11.7 Hz, 2H), 6.25-6.15 (m, 2H), 6.15-6.01 (m, 2H), 5.62 (m, 2H), 5.43-5.38 (m, 2H), 5.36 (m, 2H), 5.31-5.26 (m, 2H), 4.89 (m, 2H), 4.70 (d, J=12.3 Hz, 2H), 4.62 (m, 2H), 4.56-4.47 (m, 2H), 4.24 (m, 4H), 4.03 (m, 2H), 3.81-3.65 (m, 2H), 3.53 (t, J=11.6 Hz, 2H), 2.79 (m, 2H), 2.23-2.08 (m, 8H), 1.41 (m, 2H).

Example 21. 4,4'-bis(O(9)-benzylcinchonidium-N-methyl)biphenyl Ether Dibromide (10-1-1)

After Compound 9 (50 mg, 0.053 mmol) obtained by the method of Example 19 was suspended in dichloromethane (3 mL), a 50% potassium hydroxide solution (0.25 mL, 2.2 mmol) and benzyl bromide (0.044 mL, 0.37 mmol) were added, and then the mixture was stirred at room temperature for 2 hours. The reaction mixture was diluted with water (3 mL), and an organic layer was separated. A dichloromethane solution was dried over anhydrous magnesium sulfate and filtered. The resulting filtrate was added dropwise to ethyl ether (50 mL), thereby obtaining a solid. The obtained solid was separated and purified by column chromatography (dichloromethane/methanol) to obtain a pale orange solid (83 mg) as a desired product.

$^1$H NMR (300 MHz, DMSO-$d_6$) δ 9.87 (d, J=6.2 Hz, 2H), 8.82 (d, J=8.2 Hz, 2H), 8.60 (d, J=9.0 Hz, 2H), 8.46 (d, J=6.3 Hz, 2H), 8.30 (t, J=8.1 Hz, 2H), 8.17 (t, J=7.7 Hz, 2H), 7.83 (m, 2H), 7.61 (m, 2H), 7.43-7.38 (m, 10H), 6.90 (m, 2H), 6.50-6.41 (m, 4H), 5.71 (m, 2H), 5.24 (m, 2H), 5.16 (m, 2H), 5.01 (m, 4H), 4.40 (m, 2H), 4.22-4.15 (m, 2H), 4.03-3.88 (m, 4H), 3.38 (m, 4H), 2.72 (m, 2H), 2.30 (m, 2H), 2.02 (m, 2H), 1.85 (m, 2H), 1.60 (m, 2H), 1.25 (m, 2H), 0.86 (m, 2H).

Example 22. 4,4'-bis(hydrocinchonidium-N-methyl)biphenyl Ether Dibromide (9-2)

To a 25-mL round bottom flask, were added (−)-hydrocinchonidine] (600 mg, 2.02 mmol) and 4,4'-oxybis(bromomethyl)benzene (400 mg, 1.12 mmol) was added, and refluxed with stirring at 110° C. for 2 hours in a mixed solvent of ethanol:N,N-dimethylformamide:chloroform (5:6:2) (6 mL). The reaction mixture was cooled to room temperature and added dropwise to ether (50 mL) to precipitate a solid, followed by filtering under reduced pressure. The obtained solid was recrystallized with methanol-ether to obtain a pale yellow solid (2.346 g) as a desired product.

$^1$H NMR (300 MHz, DMSO-$d_6$) δ 8.99 (d, J=4.6 Hz, 2H), 8.31 (d, J=8.4 Hz, 2H), 8.11 (d, J=8.3 Hz, 2H), 7.89-7.70 (m, 10H), 7.27 (d, J=8.2 Hz, 4H), 6.74 (m, 2H), 6.55 (m, 2H), 5.21 (d, J=12.7 Hz, 2H), 4.95 (d, J=12.2 Hz, 2H), 4.27 (m, 2H), 3.92 (m, 2H), 3.44 (m, 2H), 3.31-3.20 (m, 4H), 2.08 (m, 4H), 1.96 (m, 2H), 1.77 (m, 4H), 1.34 (m, 2H), 1.16 (m, 4H), 0.71 (m, J=7.1 Hz, 6H).

Example 23. 4,4'-bis(O(9)-allylhydrocinchonidium-N-methyl)biphenyl Ether Dibromide (10-2)

After Compound 9-2 (150 mg, 0.16 mmol) obtained by the method of Example 22 was suspended in dichloromethane (3 mL), a 50% potassium hydroxide solution (0.25 mL, 2.2 mmol) and allyl bromide (0.09 mL, 1.10 mmol) were added, and then the mixture was stirred at room temperature for 2.5 hours. The reaction mixture was diluted with water (3 mL), and an organic layer was separated. A dichloromethane solution was dried over anhydrous magnesium sulfate and filtered. The resulting filtrate was added dropwise to ethyl ether (50 mL), thereby obtaining a solid. The obtained solid was separated and purified by column chromatography (dichloromethane/methanol) to obtain a pale orange solid (135 mg) as a desired product.

$^1$H NMR (300 MHz, Chloroform-d) δ 8.98 (d, J=4.1 Hz, 2H), 8.85 (d, J=8.5 Hz, 2H), 8.16 (d, J=8.4, 1.4 Hz, 2H), 8.00 (d, J=8.8 Hz, 4H), 7.93 (m, 2H), 7.85-7.78 (m, 4H), 7.13 (d, J=8.2 Hz, 4H), 6.45 (d, J=11.8 Hz, 2H), 6.32-6.21 (m, 2H), 6.18-6.04 (m, 2H), 5.48-5.33 (m, 4H), 4.71 (m, J=12.2 Hz, 2H), 4.61 (d, J=11.5 Hz, 2H), 4.29 (m, 4H), 4.06 (m, 2H), 3.49-3.36 (m, 2H), 3.24 (m, 2H), 2.15 (m, 4H), 2.07 (m, 2H), 1.79-1.68 (m, 4H), 1.59-1.35 (m, 6H), 1.33-1.23 (m, 2H), 0.83-0.65 (m, 6H).

Example 24. 4,4'-bis(quinium-N-methyl)biphenyl Ether Dibromide (9-3)

To a 25-mL round bottom flask, 4,4'-oxybis(bromomethyl)benzene (200 mg, 0.56 mmol) was added to (−)-quinine (328 mg, 1.01 mmol), and refluxed with stirring at 110° C. for 3 hours in a mixed solvent of ethanol:N,N-dimethylformamide:chloroform (5:6:2) (3 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (541 mg) as a desired product.

$^1$H NMR (300 MHz, DMSO-$d_6$) δ 8.82 (d, J=4.4 Hz, 2H), 8.03 (d, J=9.1 Hz, 2H), 7.76 (m, 6H), 7.50 (d, J=9.2, 2.5 Hz, 2H), 7.39 (d, J=2.6 Hz, 2H), 7.27 (d, J=8.2 Hz, 4H), 6.70 (d, J=4.2 Hz, 2H), 6.60 (m, 2H), 5.75-5.67 (m, 2H), 5.45 (d, J=12.3 Hz, 2H), 5.12 (d, J=17.3 Hz, 2H), 5.01 (d, J=10.4 Hz, 2H), 4.73 (d, J=12.3 Hz, 2H), 4.23 (m, 2H), 4.02 (s, J=6.1 Hz, 6H), 3.86 (m, 2H), 3.68 (m, 2H), 3.41 (m, 2H), 3.25 (m, 2H), 2.72 (m, 2H), 2.18 (m, 4H), 2.02 (m, 2H), 1.86 (m, 2H), 1.46 (m, J=11.7 Hz, 2H).

Example 25. 4,4'-bis(O(9)-allylquinium-N-methyl)biphenyl Ether Dibromide (10-3)

After Compound 9-3 (100 mg, 0.10 mmol) obtained by the method of Example 24 was suspended in chloroform (3 mL), a 50% potassium hydroxide solution (0.25 mL, 2.2 mmol) and allyl bromide (0.06 mL, 0.70 mmol) were added, and then the mixture was stirred at room temperature for 2 hours. The reaction mixture was diluted with water (3 mL), and an organic layer was extracted with dichloromethane (2×, 3 mL). The dichloromethane solution was dried over anhydrous magnesium sulfate and filtered, followed by vacuum evaporation. The resulting product was separated and purified by column chromatography (dichloromethane/methanol) to obtain a light brown solid (30 mg) as a desired product.

$^1$H NMR (300 MHz, Chloroform-d) δ 8.92-8.76 (m, 2H), 8.15-8.01 (m, 2H), 7.86 (d, J=8.2 Hz, 2H), 7.41 (d, J=11.5 Hz, 2H), 7.21 (d, J=9.0 Hz, 2H), 7.11 (m, 2H), 7.05-6.83 (m, 2H), 6.25-6.01 (m, 4H), 5.97-5.75 (m, 2H), 5.40 (m, 4H), 5.33-5.22 (m, 4H), 4.25 (d, J=23.5 Hz, 4H), 4.03 (m, 4H), 3.93 (m, 2H), 3.88-3.80 (m, 4H), 3.62 (m, 2H), 3.41 (m, 2H), 2.61 (m, 2H), 2.44 (m, 2H), 2.21 (m, 2H), 2.07-1.96 (m, 6H), 1.57-1.44 (m, 2H), 1.13-1.08 (m, 4H), 0.84 (m, 4H).

Example 26. 4,4'-bis(cinchonidium-N-methyl)biphenyl Thioether Dibromide (11)

To a 25-mL round bottom flask, bis(4-(bromomethyl)phenyl)sulfane (492 mg, 1.32 mmol) was added to (−)-cinchonidine (700 mg, 2.4 mmol), and refluxed with stirring at 110° C. for 4.5 hours in a mixed solvent of ethanol:N,N-dimethylformamide:chloroform (5:6:2) (5 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a bright red solid (781 mg) as a desired product.

$^1$H NMR (300 MHz, DMSO-$d_6$) δ 8.97 (d, J=4.5 Hz, 2H), 8.30 (d, J=7.9 Hz, 2H), 8.10 (d, J=8.5 Hz, 2H), 7.91-7.69 (m, 10H), 7.56 (m, 4H), 6.76 (m, 2H), 6.54 (m, 2H), 245.75 (m, 2H), 5.66 (m, 2H), 5.29-5.01 (m, 6H), 4.94 (m, 2H), 4.26 (m, 2H), 3.91 (m, 2H), 3.78 (m, 2H), 3.36 (m, 2H), 3.26 (m, 2H), 2.68 (m, 2H), 2.03 (m, 6H), 1.82 (m, 2H), 1.27 (m, 2H).

Example 26-1. 3,3'-bis(cinchonidium-N-methyl)biphenyl Sulfide Dibromide (11-1)

To a 10-mL round bottom flask, bis(3-bromomethylphenyl) sulfide (165 g, 443 mmol) was added to (−)-cinchonidine (235 mg, 798 mmol), and refluxed with stirring for 4.5 hours in a mixed solvent of ethanol:N,N-dimethylformamide:chloroform (5:6:2) (2.5 mL). The reaction mixture was cooled to room temperature and added dropwise to ether (200 mL) to precipitate a solid, followed by filtering under reduced pressure. The obtained solid was separated and purified by column chromatography (dichloromethane/methanol) to obtain a pale yellow solid (184 mg) as a desired product.

$^1$H NMR (300 MHz, DMSO-$d_6$) δ 8.98 (d, J=4.5 Hz, 2H), 8.29 (d, J=8.3 Hz, 2H), 8.15-8.01 (m, 5H), 7.84-7.73 (m, 9H), 7.54 (t, J=7.9 Hz, 2H), 6.72 (d, J=4.6 Hz, 2H), 6.52 (d, J=5.1 Hz, 2H), 5.73-5.58 (m, 2H), 5.23-5.13 (m, 4H), 5.08-5.01 (m, 2H), 4.98-4.92 (m, 2H), 4.30 (m, 2H), 3.91 (t, J=9.4 Hz, 2H), 3.82-3.71 (m, 2H), 3.39 (m, 2H), 2.69 (m, 2H), 2.17-1.97 (m, 8H), 1.82 (d, J=4.1 Hz, 2H), 1.34-1.24 (m, 2H).

Example 27. 4,4'-bis(O(9)-allylcinchonidium-N-methyl)biphenyl Thioether Dibromide (12)

After Compound 11 (150 mg, 0.156 mmol) obtained by the method of Example 26 was suspended in dichloromethane (3.5 mL), a 50% potassium hydroxide solution (0.25 mL, 2.2 mmol) and allyl bromide (133 mg, 1.10 mmol) were added, and then the mixture was stirred at room temperature for 4 hours. The reaction mixture was diluted with water (5 mL), and an organic layer was separated. A dichloromethane solution was dried over anhydrous magnesium sulfate and filtered. The obtained solid was separated and purified by column chromatography (dichloromethane/methanol) to obtain a pale orange solid (88 mg) as a desired product.

$^1$H NMR (300 MHz, Chloroform-d) δ 8.97 (d, J=7.6, 4.4 Hz, 2H), 8.85 (d, J=8.9 Hz, 2H), 8.13 (d, J=8.3, 4.8 Hz, 2H), 7.97 (m, 4H), 7.90 (m, 2H), 7.69 (m, 2H), 7.61 (m, 2H), 7.44 (d, J=8.3 Hz, 4H), 6.60 (d, J=11.9 Hz, 2H), 6.23 (m, 2H), 6.20-6.02 (m, 2H), 5.66 (m, 2H), 5.48-5.34 (m, 6H), 4.98 (d, J=10.6 Hz, 2H), 4.91 (m, 2H), 4.62 (m, 4H), 4.29 (m, 4H), 4.12-3.99 (m, 2H), 3.52-3.41 (m, 2H), 3.27 (m, 2H), 2.73 (m, 2H), 2.17 (m, 4H), 2.10 (m, 2H), 1.41 (m, 2H).

Example 27-1. 3,3'-bis(O(9)-allylcinchonidium-N-methyl)biphenyl Sulfide Dibromide (12-1)

After Compound 11-1 (72 mg, 74.9 mmol) obtained by the method of Example 26-1 was suspended in dichloromethane (1.5 mL), a 50% potassium hydroxide solution (0.2 mL, 1.78 mmol) and allyl bromide (64 mg, 525 mmol) were added, and then the mixture was stirred at room temperature for 3 hours. The reaction mixture was diluted with sodium bromide and water (5 mL), and an organic layer was separated. The organic layer was dried over anhydrous magnesium sulfate and filtered. The obtained solid was separated and purified by column chromatography (dichloromethane/methanol) to obtain a pale yellow solid (42 mg) as a desired product.

$^1$H NMR (300 MHz, Chloroform-d) δ 8.97 (d, J=4.5 Hz, 2H), 8.83 (d, J=8.7 Hz, 2H), 8.14 (dd, J=8.4, 2.9 Hz, 4H), 7.95-7.84 (m, 4H), 7.77 (t, J=7.3 Hz, 2H), 7.64 (m, 4H), 7.39 (t, J=7.9 Hz, 2H), 6.61 (d, J=12.0 Hz, 2H), 6.24 (m, 2H), 6.19-6.01 (m, 2H), 5.70 (ddd, J=17.0, 10.5, 6.2 Hz, 2H), 5.46-5.33 (m, 6H), 5.06-4.89 (m, 4H), 4.78-4.59 (m, 4H), 4.42-4.23 (m, 4H), 4.09 (m, 2H), 3.47-3.33 (m, 2H), 3.31-3.17 (m, 2H), 2.65 (m, 2H), 2.22 (m, 2H), 2.07 (m, 4H), 1.87 (m, 2H), 1.45 (m, 2H).

Example 28. 4,4'-bis(hydrocinchonidium-N-methyl)biphenyl Thioether Dibromide (11-2)

To a 25-mL round bottom flask, bis(4-(bromomethyl)phenyl)sulfane (600 mg, 1.61 mmol) was added to (−)-hydrocinchonidine (860 mg, 2.90 mmol), and refluxed with stirring at 110° C. for 2.5 hours in a mixed solvent of ethanol:N,N-dimethylformamide:chloroform (5:6:2) (8 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a yellow solid (950 mg) as a desired product.

$^1$H NMR (300 MHz, DMSO-d$_6$) δ 9.00 (d, J=4.7 Hz, 2H), 8.28 (d, J=8.2 Hz, 2H), 8.12 (d, J=8.3 Hz, 2H), 7.91-7.79 (m, 4H), 7.74 (m, 6H), 7.56 (m, 4H), 6.72 (m, 2H), 6.54 (m, 2H), 5.15 (m, 2H), 4.91 (m, 2H), 4.25 (m, 2H), 3.89 (m, 2H), 3.40 (m, 2H), 3.15 (m, 4H), 2.08 (m, 4H), 1.96 (m, 2H), 1.75 (m, 4H), 1.35 (m, 2H), 1.27-1.08 (m, 4H), 0.71 (m, 6H).

Example 29. 4,4'-bis(O(9)-allylhydrocinchonidium-N-methyl)biphenyl Thioether Dibromide (12-2)

After Compound 11-2 (152 mg, 0.157 mmol) obtained by the method of Example 28 was suspended in dichloromethane (2 mL), a 50% potassium hydroxide solution (0.25 mL, 2.2 mmol) and allyl bromide (135 mg, 1.10 mmol) were added, and then the mixture was stirred at room temperature for 2 hours. The reaction mixture was diluted with water (5 mL), and an organic layer was separated. A dichloromethane solution was dried over anhydrous magnesium sulfate and filtered. The obtained solid was purified by column chromatography (dichloromethane/methanol) to obtain a pale yellow solid (96 mg) as a desired product.

$^1$H NMR (300 MHz, Chloroform-d) δ 9.00 (d, J=4.3 Hz, 2H), 8.89 (d, J=8.7 Hz, 2H), 8.16 (d, J=8.2 Hz, 2H), 7.94 (m, 6H), 7.82 (m, 2H), 7.46 (d, J=8.5 Hz, 4H), 6.58 (d, J=11.2 Hz, 2H), 6.19 (m, 4H), 6.15-6.01 (m, 2H), 5.49-5.33 (m, 4H), 4.81 (m, 4H), 4.49 (d, J=11.3 Hz, 4H), 4.42-4.20 (m, 4H), 3.97 (m, 2H), 3.37 (m, 2H), 3.27-3.11 (m, 2H), 2.14 (m, 6H), 1.89 (m, 4H), 1.40 (m, 4H), 1.27 (m, 2H), 0.80 (t, J=7.3 Hz, 6H). total H=68.

Example 30. 4,4'-bis(quinium-N-methyl)biphenyl Thioether Dibromide (11-3)

To a 25-mL round bottom flask, bis(4-(bromomethyl)phenyl)sulfane (127 mg, 0.343 mmol) was added to (−)-quinine (200 mg, 0.616 mmol), and refluxed with stirring at 110° C. for 2.5 hours in a mixed solvent of ethanol:N,N-dimethylformamide:chloroform (5:6:2) (3 mL). The reaction mixture was cooled to room temperature and added dropwise to ether (25 mL) to precipitate a solid, followed by filtering under reduced pressure. Then, an orange solid (320 mg) was obtained as a desired product.

$^1$H NMR (300 MHz, DMSO-d$_6$) δ 8.82 (d, J=4.5 Hz, 2H), 8.03 (d, J=9.0 Hz 2H), 7.80-7.69 (m, 6H), 7.52 (d, J=8.1 Hz, 4H), 7.50 (m, 2H), 7.38 (d, J=3.2 Hz, 2H), 6.70 (d, J=4.1 Hz, 2H), 6.59 (m, 2H), 5.85-5.66 (m, 2H), 5.45 (d, J=12.4 Hz, 2H), 5.12 (d, J=17.3 Hz, 2H), 5.01 (d, J=10.3 Hz, 2H), 4.73 (d, J=12.5 Hz, 2H), 4.29-4.07 (m, 2H), 4.01 (s, 6H), 4.00-3.97 (m, 2H), 3.83 (m, 2H), 3.67 (m, 2H), 3.23 (m, 2H), 2.68 (m, 2H), 2.17 (m, 4H), 2.01 (m, 2H), 1.84 (m, 2H), 1.46 (m, 2H).

Example 31. 4,4'-bis(O(9)-allylquinium-N-methyl)biphenyl Thioether Dibromide (12-3)

After Compound 11-3 (100 mg, 0.10 mmol) obtained by the method of Example 30 was suspended in dichloromethane (1 mL), a 50% potassium hydroxide solution (0.25 mL, 2.23 mmol) and allyl bromide (82 mg, 0.67 mmol) were added, and then the mixture was stirred at room temperature for 5 hours. The reaction mixture was diluted with sodium bromide and water (5 mL), and an organic layer was separated. A dichloromethane solution was dried over anhydrous magnesium sulfate and filtered. The obtained solid was separated and purified by column chromatography (dichloromethane/methanol) to obtain a pale yellow solid (39.4 mg) as a desired product.

$^1$H NMR (300 MHz, DMSO-d$_6$) δ 8.84 (d, J=4.5 Hz, 2H), 8.04 (d, J=9.1 Hz, 2H), 7.78 (d, J=8.4 Hz, 4H), 7.65 (d, J=4.5 Hz, 2H), 7.58 (d, J=8.3 Hz, 4H), 7.51 (dd, J=9.2, 2.6 Hz, 2H), 7.43 (m, 2H), 6.58 (m, 2H), 6.14 (m, 2H), 5.88-5.56 (m, 8H), 5.54-5.40 (m, 2H), 5.28 (m, 2H), 5.15-4.96 (m, 4H), 4.81 (d, J=11.8 Hz, 2H), 4.51 (m, 2H), 4.02-3.89 (m, 10H), 2.72 (m, 2H), 2.38 (d, J=12.8 Hz, 2H), 2.25-2.13 (m, 2H), 2.07-2.00 (m, 2H), 1.91 (m, 2H), 1.64-1.48 (m, 2H), 1.22 (m, 2H).

Example 32. 4,4'-bis(cinchonidium-N-methyl)biphenyl Sulfoxide Dibromide (13)

To a 25-mL round bottom flask, 4,4'-sulfinylbis(bromomethyl)benzene (200 mg, 0.815 mmol) was added to (−)-cinchonidine (272 mg, 1.38 mmol), and refluxed with stirring at 110° C. for 3 hours in a mixed solvent of ethanol:N,N-dimethylformamide:chloroform (5:6:2) (3 mL). The reaction mixture was cooled to room temperature and added dropwise to ether (20 mL) to precipitate a solid, followed by filtering under reduced pressure. From the obtained solid, a pale orange solid (320 mg) was obtained as a desired product.

$^1$H NMR (300 MHz, DMSO-d$_6$) δ 8.98 (d, J=4.4 Hz, 2H), 8.33 (m, 2H), 8.10 (d, J=8.4 Hz, 2H), 7.90-7.65 (m, 10H), 7.57 (d, J=8.3 Hz, 4H), 6.78 (d, J=4.7 Hz, 2H), 6.56 (m, 2H), 5.65 (m, 2H), 5.32-5.09 (m, 6H), 4.99-4.89 (m, 2H), 4.31 (m, 2H), 3.95 (m, 2H), 3.84 (m, 2H), 3.41-3.26 (m, 4H), 2.70 (m, 2H), 2.18-1.96 (m, 6H), 1.88-1.80 (m, 2H), 1.26 (m, 2H).

Example 33. 4,4'-bis(O(9)-allylcinchonidium-N-methyl)biphenyl Sulfoxide Dibromide (14)

After Compound 13 (85 mg, 0.0804 mmol) obtained by the method of Example 32 was suspended in chloroform (2 mL), a 50% potassium hydroxide solution (0.08 mL, 0.704 mmol) and allyl bromide (68 mg, 0.563 mmol) were added, and then the mixture was stirred at room temperature for 5 hours. The reaction mixture was diluted with NaBr (5 mL) and water (5 mL), and an organic layer was separated. A chloroform solution was dried over anhydrous magnesium sulfate and filtered. The obtained solid was separated and purified by column chromatography (dichloromethane/methanol) to obtain a pale yellow solid (30 mg) as a desired product.

$^1$H NMR (300 MHz, DMSO-$d_6$) δ 9.01 (d, J=4.5, 4.0 Hz, 2H), 8.29 (d, J=8.4 Hz, 2H), 8.14 (d, J=8.3 Hz, 2H), 7.94-7.73 (m, 8H), 7.69 (d, J=7.9 Hz, 2H), 7.62-7.54 (m, 4H), 6.45 (s, 2H), 6.16 (m, 2H), 5.80-5.61 (m, 2H), 5.69 (m, 2H), 5.34-5.24 (m, 2H), 5.29 (m, 2H), 5.22-5.09 (m, 4H), 5.00 (m, 4H), 4.38 (m, 2H), 4.03 (m, 6H), 3.77 (m, 2H), 3.55-3.25 (m, 4H), 2.71 (m, 2H), 2.28 (m, 2H), 2.11 (m, 2H), 2.03 (m, 2H), 1.88 (m, 2H), 1.43 (m, 2H).

Example 34.
4,4'-bis(hydrocinchonidium-N-methyl)biphenyl Sulfoxide Dibromide (13-1)

To a 25-mL round bottom flask, 4,4'-sulfinylbis(bromomethyl)benzene (300 mg, 0.815 mmol) was added to (−)-hydrocinchonidine (411 mg, 1.39 mmol), and refluxed with stirring at 110° C. for 5.5 hours in a mixed solvent of ethanol:N,N-dimethylformamide:chloroform (5:6:2) (3 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale orange solid (150 mg) as a desired product.

$^1$H NMR (300 MHz, DMSO-$d_6$) δ 8.98 (d, J=4.5 Hz, 2H), 8.31 (m, 2H), 8.10 (m, 2H), 7.90-7.62 (m, 10H), 7.61-7.36 (m, 4H), 6.76 (m, 2H), 6.55 (m, 2H), 5.25 (m, 2H), 5.01 (m, 2H), 4.31 (m, 2H), 3.94 (m, 2H), 3.50 (m, 2H), 3.38-3.29 (m, 4H), 2.07 (m, 4H), 1.94 (m, 2H), 1.76 (m, 4H), 1.33 (m, 2H), 1.16 (m, 4H), 0.75-0.62 (m, 6H).

Example 35. 4,4'-bis(O(9)-allylhydrocinchonidium-N-methyl)biphenyl Sulfoxide Dibromide (14-1)

After Compound 13-1 (148 mg, 0.140 mmol) obtained by the method of Example 34 was suspended in methylene chloride (1.5 mL), a 50% potassium hydroxide solution (0.25 mL, 2.2 mmol) and allyl bromide (119 mg, 0.980 mmol) were added, and then the mixture was stirred at room temperature for 0.5 hours. The reaction mixture was diluted with NaBr (5 mL) and water (5 mL), and an organic layer was separated. A dichloromethane solution was dried over anhydrous magnesium sulfate and filtered. The obtained solid was purified by column chromatography (dichloromethane/methanol) to obtain a pale yellow solid (105 mg) as a desired product.

$^1$H NMR (300 MHz, DMSO-$d_6$) δ 9.02 (d, J=4.4 Hz, 2H), 8.27 (d, J=8.4 Hz, 2H), 8.14 (d, J=8.4 Hz, 2H), 7.88 (m, 2H), 7.83-7.49 (m, 14H), 6.43 (m, 2H), 6.15 (m, 2H), 5.52-5.37 (m, 2H), 5.29 (m, 2H), 5.15 (m, 2H), 4.92 (m, 2H), 4.37 (m, 2H), 3.99 (m, 4H), 3.29-3.14 (m, 4H), 2.26 (m, 2H), 2.08 (m, 2H), 1.98 (m, 2H), 1.79 (m, 4H), 1.47 (m, 4H), 1.18 (m, 4H), 0.70 (t, 6H).

Example 36.
4,4'-bis(cinchonidium-N-methyl)biphenyl Sulfone Dibromide (15)

To a 25-mL round bottom flask, 4,4'-sulfonylbis((bromomethyl)benzene) (268 mg, 0.663 mmol) was added to (−)-cinchonidine (332 mg, 1.27 mmol), and refluxed with stirring at 110° C. for 4 hours in a mixed solvent of ethanol:N,N-dimethylformamide:chloroform (5:6:2) (6 mL). The reaction mixture was cooled to room temperature and added dropwise to ether (100 mL) to precipitate a solid, followed by filtering under reduced pressure. The obtained solid was separated and purified by column chromatography (dichloromethane/methanol) to obtain a bright red solid (576 mg) as a desired product.

$^1$H NMR (300 MHz, DMSO-$d_6$) δ 8.96 (d, J=4.6 Hz, 2H), 8.25 (m, 6H), 8.07 (m, 6H), 7.92-7.76 (m, 4H), 7.71 (m, 2H), 6.79 (d, J=4.9 Hz, 2H), 6.52 (m, 2H), 6.60-6.42 (m, 4H), 5.65 (m, 2H), 5.28 (m, 2H), 5.15 (m, 2H), 4.93 (m, 2H), 4.29 (m, 2H), 3.92 (m, 2H), 3.77 (m, 2H), 3.25 (m, 2H) 2.64 (m, 2H), 2.19-1.91 (m, 8H), 1.78 (m, 2H), 1.23 (m, 2H).

Example 37. 4,4'-bis(O(9)-allylcinchonidium-N-methyl)biphenyl Sulfone Dibromide (16)

After Compound 15 (50 mg, 0.05 mmol) obtained by the method of Example 36 was suspended in dichloromethane (1 mL), a 50% potassium hydroxide solution (0.20 mL, 1.78 mmol) and allyl bromide (43 mg, 0.35 mmol) were added, and then the mixture was stirred at room temperature for 2.5 hours. The reaction mixture was diluted with sodium bromide and water (5 mL), and an organic layer was separated. A dichloromethane solution was dried over anhydrous magnesium sulfate and filtered. The obtained solid was separated and purified by column chromatography (dichloromethane/methanol) to obtain a pale yellow solid (27 mg) as a desired product.

1H NMR (300 MHz, Chloroform-d) δ 8.96 (d, J=4.4 Hz, 2H), 8.69 (d, J=8.6 Hz, 2H), 8.29-7.97 (m, 10H), 7.72 (m, 6H), 6.30 (d, J=7.4 Hz, 4H), 6.11 (m, 10.6, 5.8 Hz, 2H), 5.59 (m, 2H), 5.45-5.24 (m, 6H), 4.93 (m, 4H), 4.51 (d, J=13.1 Hz, 2H), 4.40 (d, J=13.4 Hz, 4H), 4.29 (d, J=8.6 Hz, 2H), 4.22 (d, J=6.0 Hz, 4H), 3.67-3.33 (m, 4H), 2.77 (m, 2H), 2.05 (m, 6H), 1.48-1.34 (m, 2H).

Example 38.
4,4'-bis(hydrocinchonidium-N-methyl)biphenyl Sulfone Dibromide (15-1)

To a 25-mL round bottom flask, 4,4'-sulfonylbis(bromomethyl)benzene (500 mg, 1.24 mmol) was added to (−)-hydrocinchonidine (660 mg, 2.23 mmol), and refluxed with stirring at 110° C. for 4.5 hours in a mixed solvent of ethanol:N,N-dimethylformamide:chloroform (5:6:2) (5 mL). The reaction mixture was cooled to room temperature and added dropwise to ether (40 mL) to precipitate a solid, followed by filtering under reduced pressure. The obtained solid was separated and purified by column chromatography (dichloromethane/methanol) to obtain a pale yellow solid (253 mg) as a desired product.

$^1$H-NMR (300 MHz, DMSO-$d_6$) δ 8.98 (d, J=4.5 Hz, 2H), 8.26 (m, 6H), 8.07 (m, 6H), 7.83 (m, 4H), 7.72 (m, 2H), 6.72 (m, 2H), 6.53 (m, 2H), 5.31 (d, J=12.2 Hz, 2H), 5.07 (d, J=12.2 Hz, 2H), 4.32 (m, 2H), 3.95 (m, 2H), 3.50 (m, 2H), 3.26 (m, 4H), 2.24-1.99 (m, 4H), 1.94 (m, 2H), 1.74 (m, 4H), 1.34 (m, 2H), 1.16 (m, 4H), 0.70 (m, 6H).

Example 39. 4,4'-bis(O(9)-allylhydrocinchonidium-N-methyl)biphenyl Sulfone Dibromide (16-1)

After Compound 15-1 (300 mg, 0.31 mmol) obtained by the method of Example 38 was suspended in dichloromethane (10 mL), a 50% potassium hydroxide solution (0.35 mL, 3.1 mmol) and allyl bromide (0.16 mL, 1.9 mmol) were added, and then the mixture was stirred at room temperature for 2 hours. The reaction mixture was diluted with water (5 mL), and an organic layer was separated. A dichloromethane solution was dried over anhydrous magnesium sulfate and filtered. The resulting filtrate was added dropwise to ether (50 mL) to precipitate a solid, followed by filtering under reduced pressure. The obtained solid was separated and purified by column chromatography (dichloromethane/methanol) to obtain a pale orange solid (270 mg) as a desired product.

$^1$H NMR (300 MHz, Chloroform-d) δ 8.96 (d, J=4.5 Hz, 2H), 8.70 (d, J=8.4 Hz, 2H), 8.22-8.19 (m, 4H), 8.14-8.11 (m, 2H), 8.00 (d, J=8.2 Hz, 4H), 7.89-7.55 (m, 6H), 6.28 (m, 4H), 6.21-5.98 (m, 2H), 5.48-5.31 (m, 4H), 4.89 (d, J=11.7 Hz, 2H), 4.52 (m, 2H), 4.38 (m, 4H), 4.21 (m, 4H), 3.56-3.35 (m, 2H), 3.27 (m, 2H), 2.17 (m, 4H), 2.03 (m, 2H), 1.91 (m, 4H), 1.51-1.29 (m, 4H), 1.29-1.05 (m, 2H), 0.73 (m, 6H).

Example 40.
4,4'-bis(cinchonium-N-methyl)biphenyl Methanone Dibromide (17)

To a 25-mL round bottom flask, bis(4-(bromomethyl)phenyl)methanone (101 mg, 0.27 mmol) was added to (+)-cinchonine (144 mg, 0.49 mmol), and refluxed with stirring at 110° C. for 4 hours in a mixed solvent of ethanol:N,N-dimethylformamide:chloroform (5:6:2) (5 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale yellow solid (223 mg) as a desired product.

$^1$H NMR (300 MHz, DMSO-d$_6$) δ 9.01 (d, J=4.6 Hz, 2H), 8.38 (d, J=8.7 Hz, 2H), 8.17-8.08 (m, 2H), 7.99 (m, 6H), 7.92-7.71 (m, 8H), 6.89 (m, 2H), 6.55 (m, 2H), 6.06-5.94 (m, 2H), 5.31-5.18 (m, 6H), 5.05 (d, J=12.5 Hz, 2H), 4.28 (m, 2H), 3.98-3.78 (m, 4H), 3.52 (m, 2H), 3.06 (m, 2H), 2.66 (m, 2H), 2.30 (m, 2H), 1.84-1.72 (m, 6H), 1.09 (m, 2H).

Example 41. 4,4'-bis(O(9)-allylcinchonium-N-methyl)biphenyl Methanone Dibromide (18)

After Compound 17 (50 mg, 0.052 mmol) obtained by the method of Example 40 was suspended in dichloromethane (3 mL), a 50% potassium hydroxide solution (0.25 mL, 2.2 mmol) and allyl bromide (38 mg, 0.31 mmol) were added, and then the mixture was stirred at room temperature for 2 hours. The reaction mixture was diluted with water (5 mL), and an organic layer was extracted with dichloromethane (2×, 20 mL). The dichloromethane solution was dried over anhydrous magnesium sulfate and filtered, followed by vacuum evaporation. The resulting product was separated and purified by column chromatography (dichloromethane/methanol) to obtain a pale orange solid (42 mg) as a desired product.

$^1$H NMR (300 MHz, DMSO-d$_6$) δ 9.00 (d, J=4.5 Hz, 2H), 8.98-8.81 (m, 2H), 8.16 (m, 6H), 8.01-7.74 (m, 10H), 6.72 (d, J=10.8 Hz, 2H), 6.23 (m, 2H), 6.20-6.06 (m, 2H), 5.99-5.84 (m, 2H), 5.44-5.20 (m, 12H), 4.55 (d, J=11.7 Hz, 2H), 4.40-4.18 (m, 6H), 4.04 (dd, J=11.9, 6.2 Hz, 2H), 3.58 (m, 2H), 2.91 (m, 2H), 2.60 (m, 2H), 2.37 (m, 2H), 2.01-1.88 (m, 4H) 1.13 (m, 2H).

Example 42.
4,4'-bis(cinchonium-N-methyl)biphenyl Methane Dibromide (19)

To a 25-mL round bottom flask, bis(4-(bromomethyl)phenyl)methane (300 mg, 0.847 mmol) was added to (+)-cinchonine (449 mg, 1.52 mmol), and refluxed with stirring at 110° C. for 5 hours in a mixed solvent of ethanol:N,N-dimethylformamide:chloroform (5:6:2) (4 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pink solid (468 mg) as a desired product.

$^1$H NMR (300 MHz, DMSO-d$_6$) δ 8.98 (d, J=4.5 Hz, 2H), 8.37 (d, J=7.4 Hz, 2H), 8.10 (dd, J=8.4, 1.5 Hz, 2H), 7.87-7.79 (m, 4H), 7.79-7.69 (m, 6H), 7.50 (d, J=8.3 Hz, 4H), 6.82 (d, J=4.4 Hz, 2H), 6.56-6.47 (m, 2H), 6.11-5.92 (m, 2H), 5.25 (m, 2H), 5.21 (m, 2H), 5.15 (m, 2H), 5.04 (d, J=12.4 Hz, 2H), 4.25 (t, J=9.5 Hz, 2H), 4.15 (s, 2H), 4.04-3.87 (m, 4H), 3.49 (t, J=11.3 Hz, 2H), 3.06-2.91 (m, 2H), 2.75-2.59 (m, 2H), 2.35-2.22 (m, 2H), 1.88 (m, 2H), 1.83-1.69 (m, 4H), 1.11-0.95 (m, 2H).

Example 43. 4,4'-bis(O(9)-allylcinchonium-N-methyl)biphenyl Methane Dibromide (20)

After Compound 19 (200 mg, 0.212 mmol) obtained by the method of Example 42 was suspended in dichloromethane (7 mL), a 50% potassium hydroxide solution (0.35 mL, 3.1 mmol) and allyl bromide (181 mg, 1.48 mmol) were added, and then the mixture was stirred at room temperature for 1.5 hours. The reaction mixture was diluted with water (5 mL), and an organic layer was separated. A dichloromethane solution was dried over anhydrous magnesium sulfate and filtered. After vacuum distillation, the obtained solid was purified by column chromatography (dichloromethane/methanol) to obtain a pale yellow solid (114 mg) as a desired product.

$^1$H NMR (300 MHz, Chloroform-d) δ 8.98 (d, J=4.5 Hz, 2H), 8.94 (d, J=7.6 Hz, 2H), 8.15 (dd, J=8.5, 1.3 Hz, 2H), 8.03-7.58 (m, 10H), 7.29 (d, J=8.5 Hz, 4H), 6.49 (d, J=11.2 Hz, 2H), 6.22-6.16 (m, 2H), 6.10 (m, 2H), 5.92 (m, 2H), 5.46-5.47-5.22 (m, 12H), 4.70 (m, 2H), 4.43 (d, J=11.9 Hz, 2H), 4.33-4.15 (m, 4H), 4.08 (s, 2H), 3.97 (m, 2H), 3.60 (t, J=11.9 Hz, 2H), 2.96-2.79 (m, 2H), 2.62 (q, J=8.3 Hz, 2H), 2.36 (t, J=12.1 Hz, 2H), 1.99-1.88 (m, 4H), 1.10 (m, 2H).

Example 44. 4,4'-bis(quinidium-N-methyl)biphenyl Methane Dibromide (19-1)

To a 25-mL round bottom flask, bis(4-(bromomethyl)phenyl)methane (200 mg, 0.565 mmol) was added to (+)-quinidine (330 mg, 1.02 mmol), and refluxed with stirring at 110° C. for 4 hours in a mixed solvent of ethanol:N,N-dimethylformamide:chloroform (5:6:2) (4 mL). The reaction mixture was cooled to room temperature and added dropwise to ether (200 mL) to precipitate a solid, followed by filtering under reduced pressure. The obtained solid was separated and purified by column chromatography (dichloromethane/methanol) to obtain a pale yellow solid (202 mg) as a desired product.

1H NMR (300 MHz, DMSO-d$_6$) δ 8.80 (d, J=4.5 Hz, 2H), 8.01 (d, J=9.1 Hz, 2H), 7.77 (d, J=4.5 Hz, 2H), 7.69 (d, J=8.2 Hz, 4H), 7.53-7.39 (m, 8H), 6.81 (d, J=4.2 Hz, 2H), 6.54 (d, J=4.9 Hz, 2H), 6.13-5.95 (m, 2H), 5.30-5.18 (m, 4H), 5.15 (d, J=12.6 Hz, 2H), 4.77 (d, J=12.8 Hz, 2H), 4.32-4.18 (m, 2H), 4.14 (s, 2H), 4.06 (m, 8H), 3.89 (t, J=9.1 Hz, 2H), 3.50 (t, J=11.4 Hz, 2H), 3.03-2.86 (m, 2H), 2.69 (m, 2H), 2.47-2.34 (m, 2H), 1.94-1.87 (m, 2H), 1.84-1.68 (m, 4H).

Example 45. 4,4'-bis(O(9)-allylquinidium-N-methyl)biphenyl Methane Dibromide (20-1)

After Compound 19-1 (100 mg, 0.100 mmol) obtained by the method of Example 44 was suspended in dichloromethane (3 mL), a 50% potassium hydroxide solution (0.35 mL, 3.1 mmol) and allyl bromide (101 mg, 0.828 mmol) were added, and then the mixture was stirred at room temperature for 3 hours. The reaction mixture was diluted with water (5 mL), and an organic layer was separated. A dichloromethane solution was dried over anhydrous magnesium sulfate and filtered. The resulting product was separated and purified by column chromatography (dichloromethane/methanol) to obtain a pale yellow solid (63 mg) as a desired product.

1H NMR (300 MHz, Chloroform-d) δ 8.82 (d, J=4.5 Hz, 2H), 8.04 (d, J=9.2 Hz, 2H), 7.81 (d, J=7.9 Hz, 6H), 7.40 (dd, J=9.3, 2.7 Hz, 2H), 7.30 (d, J=7.5 Hz, 4H), 6.18-6.01 (m, 4H), 5.92 (m, 2H), 5.50-5.25 (m, 8H), 4.26-4.10 (m, 6H), 4.08 (s, 2H), 4.02 (dd, J=12.7, 6.2 Hz, 4H), 3.60 (t, J=11.6 Hz, 2H), 2.85 (q, J=9.8 Hz, 2H), 2.70-2.45 (m, 4H), 2.07-1.80 (m, 8H), 1.53 (m, 6H), 1.26 (m, 6H).

Example 46. 4,4'-bis(cinchonium-N-methyl)biphenyl Methanol Dibromide (21)

To a 25-mL round bottom flask, bis(4-(bromomethyl)phenyl)methanol (50 mg, 0.135 mmol) as added to (+)-cinchonine (75.5 mg, 0.256 mmol), and refluxed with stirring at 110° C. for 4 hours in a mixed solvent of ethanol:N,N-dimethylformamide:chloroform (5:6:2) (4 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale yellow solid (53 mg) as a desired product.

$^1$H NMR (300 MHz, DMSO-$d_6$) δ 8.98 (d, J=4.5 Hz, 2H), 8.35 (d, J=8.5 Hz, 2H), 8.10 (m, 2H), 7.84 (m, 4H), 7.75 (d, J=7.8 Hz, 6H), 7.64 (d, J=7.9 Hz, 4H), 6.85 (d, J=4.1 Hz, 2H), 6.50 (m, 2H), 6.23 (d, J=4.4 Hz, 1H), 6.00 (m, 2H), 5.31-5.16 (m, 4H), 5.12 (d, J=12.2 Hz, 2H), 4.95 (d, J=12.5 Hz, 2H), 4.23 (m, 2H), 4.05 (s, 1H), 3.94 (m, 4H), 3.48 (d, J=11.4 Hz, 2H), 2.99-2.81 (m, 2H), 2.65 (d, J=9.2 Hz, 2H), 2.27 (m, 2H), 1.86 (m, 2H), 1.75 (m, 4H), 1.03 (m, 2H).

Example 47. 4,4'-bis(O(9)-allylcinchonium-N-methyl)biphenyl Methanol Dibromide (22)

Compound 21 (30 mg, 0.0313 mmol) obtained by the method of Example 46 was suspended in dichloromethane (0.5 mL), a 50% potassium hydroxide solution (0.05 mL, 1.35 mmol) and allyl bromide (39.7 mg, 0.329 mmol) were added, and then the mixture was stirred at room temperature for 3 hours. The reaction mixture was diluted with water (5 mL), and an organic layer was separated. A dichloromethane solution was dried over anhydrous magnesium sulfate and filtered. The resulting product was purified by column chromatography (dichloromethane/methanol) to obtain a pale yellow solid (20 mg) as a desired product.

1H NMR (300 MHz, Chloroform-d) δ 8.98 (d, J=4.3 Hz, 2H), 8.96-8.88 (m, 2H), 8.15 (d, J=8.7 Hz, 2H), 7.99-7.92 (m, 4H), 7.85-7.76 (m, 4H), 7.56 (d, J=8.1 Hz, 2H), 7.51-7.46 (m, 4H), 6.59-6.44 (m, 2H), 6.18 (d, J=6.8 Hz, 2H), 6.10-6.00 (m, 2H), 6.00-5.95 (m, 1H), 5.95-5.87 (m, 2H), 5.55 (s, 1H), 5.42-5.36 (m, 4H), 5.17-5.10 (m, 4H), 4.66 (m, 2H), 4.44 (m, 4H), 4.31-4.15 (m, 4H), 4.04 (m, 4H), 3.59 (d, J=10.6 Hz, 2H), 3.49 (m, 2H), 2.63 (m, 2H), 1.95 (d, J=20.1 Hz, 8H), 1.79 (d, J=9.9 Hz, 2H), 1.41 (d, J=19.8 Hz, 2H), 1.26 (m, 2H).

Example 48. 4,4'-bis(cinchonium-N-methyl)biphenyl Ether Dibromide (23)

To a 25-mL round bottom flask, 4,4'-oxybis((bromomethyl)benzene) (200 mg, 0.56 mmol) was added to (+)-cinchonine (314 mg, 1.077 mmol), and refluxed with stirring at 110° C. for 3 hours in a mixed solvent of ethanol:N,N-dimethylformamide:chloroform (5:6:2) (3 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a pale pink solid (768 mg) as a desired product.

$^1$H NMR (300 MHz, DMSO-$d_6$) δ 9.00 (d, J=4.4 Hz, 2H), 8.36 (d, J=8.5 Hz, 2H), 8.12 (d, J=8.4 Hz, 2H), 7.93-7.67 (m, 10H), 7.28 (d, J=8.3 Hz, 4H), 6.82 (d, J=3.7 Hz, 2H), 6.53 (m, 2H), 6.13-5.93 (m, 2H), 5.27 (s, 2H), 5.22 (d, J=6.9 Hz, 2H), 5.13 (d, J=12.3 Hz, 2H), 4.93 (d, J=12.6 Hz, 2H), 4.21 (t, J=10.1 Hz, 2H), 3.93 (m, 4H), 3.49 (m, 2H), 3.00 (m, 2H), 2.67 (m, 2H), 2.30 (t, J=11.5 Hz, 2H), 1.84 (m, 6H), 1.10-1.05 (m, 2H).

Example 49. 4,4'-bis(O(9)-allylcinchonium-N-methyl)biphenyl Ether Dibromide (24)

Compound 23 (200 mg, 0.21 mmol) obtained by the method of Example 48 was suspended in dichloromethane (3 mL), a 50% potassium hydroxide solution (0.25 mL, 2.2 mmol) and allyl bromide (0.12 mL, 1.47 mmol) were added, and then the mixture was stirred at room temperature for 1.5 hours. The reaction mixture was diluted with water (3 mL), and an organic layer was separated. A dichloromethane solution was dried over anhydrous magnesium sulfate and filtered, followed by vacuum evaporation. The resulting product was separated and purified by column chromatography (dichloromethane/methanol) to obtain a desired product (270 mg) as an orange solid.

$^1$H NMR (300 MHz, Chloroform-d) δ 8.99 (d, J=4.4 Hz, 2H), 8.95 (d, J=8.4 Hz, 2H), 8.15 (d, J=8.4, 1.3 Hz, 2H), 8.02-7.98 (m, 8H), 7.81 (m, 2H), 7.17-7.10 (m, 4H), 6.57 (d, J=11.8 Hz, 2H), 6.21 (m, 2H), 6.13-6.06 (m, 2H), 5.97-5.87 (m, 2H), 5.47-5.24 (m, 12H), 4.47 (d, J=11.9 Hz, 2H), 4.35-4.11 (m, 6H), 4.05-3.97 (m, 2H), 3.62 (m, 2H), 2.90 (m, 2H), 2.65 (m, 2H), 2.38 (m, 2H), 1.95 (m, 4H), 1.11 (m, 2H).

Example 50. 4,4'-bis(quinidium-N-methyl)biphenyl Ether Dibromide (23-1)

To a 25-mL round bottom flask, 4,4'-oxybis((bromomethyl)benzene) (200 mg, 0.56 mmol) was added to (+)-quinidine (328.0 mg, 1.01 mmol), and refluxed with stirring at 110° C. for 4 hours in a mixed solvent of ethanol:N,N-dimethylformamide:chloroform (5:6:2) (3 mL). The reaction mixture was cooled to room temperature and added dropwise to ether (50 mL) to precipitate a solid, followed by filtering under reduced pressure. The obtained solid was separated and purified by column chromatography (dichloromethane/methanol) to obtain a light gray solid (636 mg) as a desired product.

$^1$H NMR (300 MHz, DMSO-$d_6$) δ 8.81 (d, J=4.5 Hz, 2H), 8.01 (d, J=9.2 Hz, 2H), 7.95 (m, 2H), 7.82-7.72 (m, 4H), 7.61-7.37 (m, 8H), 6.86 (d, J=3.7 Hz, 2H), 6.52 (m, 2H), 6.04-5.98 (m, 2H), 5.30-5.18 (m, 4H), 5.09 (d, J=12.6 Hz, 2H), 4.76 (d, J=12.6 Hz, 2H), 4.22 (m, 2H), 4.07 (s, 6H), 3.98 (m, 2H), 3.83 (m, 2H), 3.48 (m, 2H), 3.04-2.91 (m, 2H), 2.72 (m, 2H), 2.38 (m, 2H), 1.90 (m, 2H), 1.77 (m, 4H), 1.11 (m, 2H).

Example 51. 4,4'-bis(O(9)-allylquinidium-N-methyl)biphenyl Ether Dibromide (24-1)

Compound 23-1 (100 mg, 0.10 mmol) obtained by the method of Example 50 was suspended in chloroform (3 mL), a 50% potassium hydroxide solution (0.25 mL, 2.2 mmol) and allyl bromide (0.06 mL, 0.70 mmol) were added, and then the mixture was stirred at room temperature for 2 hours. The reaction mixture was diluted with water (3 mL), and an organic layer was extracted with dichloromethane (2×3 mL). The dichloromethane solution was dried over anhydrous magnesium sulfate and filtered, followed by vacuum evaporation. The resulting product was separated and purified by column chromatography (dichloromethane/methanol) to obtain a light brown solid (33 mg) as a desired product.
$^1$H NMR (300 MHz, Chloroform-d) δ 8.92-8.76 (m, 2H), 8.15-8.01 (m, 2H), 7.86 (d, J=8.2 Hz, 2H), 7.41 (d, J=11.5 Hz, 2H), 7.21 (d, J=9.0 Hz, 2H), 7.11 (m, 2H), 7.05-6.83 (m, 2H), 6.25-6.01 (m, 4H), 5.97-5.75 (m, 2H), 5.40 (m, 4H), 5.33-5.22 (m, 4H), 4.25 (d, J=23.5 Hz, 4H), 4.03 (m, 4H), 3.93 (m, 2H), 3.88-3.80 (m, 4H), 3.62 (m, 2H), 3.41 (m, 2H), 2.61 (m, 2H), 2.44 (m, 2H), 2.21 (m, 2H), 2.07-1.96 (m, 6H), 1.57-1.44 (m, 2H), 1.13-1.08 (m, 4H), 0.84 (m, 4H).

Example 52. 4,4'-bis(cinchonium-N-methyl)biphenyl Thioether Dibromide (25)

To a 25-mL round bottom flask, bis(4-(bromomethyl)phenyl)sulfane (140 mg, 0.38 mmol) was added to (+)-cinchonine (200 mg, 0.68 mmol), and refluxed with stirring at 110° C. for 2.5 hours in a mixed solvent of ethanol:N,N-dimethylformamide:chloroform (5:6:2) (3 mL). The reaction mixture was cooled to room temperature and added dropwise to ether (25 mL) to precipitate a solid, followed by filtering under reduced pressure. The obtained solid was separated and purified by column chromatography (dichloromethane/methanol) to obtain a cream-colored solid (74 mg) as a desired product.
$^1$H NMR (300 MHz, DMSO-$d_6$) δ 9.00 (d, J=4.5 Hz, 2H), 8.35 (d, J=9.0 Hz, 2H), 8.12 (d, J=8.5 Hz, 2H), 7.92-7.70 (m, 10H), 7.58 (d, J=8.2 Hz, 4H), 6.82 (m, 2H), 6.52 (m, 2H), 6.01 (m, 2H), 5.32-5.18 (m, 4H), 5.14 (m, 2H), 4.94 (d, J=12.4 Hz, 2H), 4.22 (m, 2H), 3.92 (m, 4H), 3.49 (t, J=11.1 Hz, 2H), 3.00 (m, 2H), 2.67 (m, 2H), 2.29 (m, 2H), 1.83 (m, 6H), 1.07 (m, 2H).

Example 53. 4,4'-bis(O(9)-allylcinchonium-N-methyl)biphenyl Thioether Dibromide (26)

Compound 25 (150 mg, 0.156 mmol) obtained by the method of Example 52 was suspended in dichloromethane (2 mL), a 50% potassium hydroxide solution (0.25 mL, 2.2 mmol) and allyl bromide (133 mg, 1.09 mmol) were added, and then the mixture was stirred at room temperature for 2.5 hours. The reaction mixture was diluted with water (5 mL), and an organic layer was extracted with dichloromethane (2×2 mL). The dichloromethane solution was dried over anhydrous magnesium sulfate and filtered, followed by vacuum evaporation. The obtained solid was purified by column chromatography (dichloromethane/methanol) to obtain a yellow solid (61 mg) as a desired product.
$^1$H NMR (300 MHz, Chloroform-d) δ 9.00 (m, 4H), 8.16 (d, J=9.1 Hz, 2H), 7.97 (m, 6H), 7.83 (m, 4H), 7.47 (d, J=8.6 Hz, 4H), 6.63 (m, 2H), 6.26-6.01 (m, 4H), 5.93 (m, 2H), 5.52-5.32 (m, 12H), 4.36-4.14 (m, 8H), 3.96 (m, 2H), 3.59 (m, 2H), 2.90 (m, 2H), 2.65 (m, 2H), 2.36 (m, 2H), 1.99 (m, 4H), 1.12 (m, 2H).

Example 54. 4,4'-bis(quinidium-N-methyl)biphenyl Thioether Dibromide (25-1)

To a 25-mL round bottom flask, bis(4-(bromomethyl)phenyl)sulfane (127 mg, 0.343 mmol) was added to (+)-quinidine (200 mg, 0.617 mmol), and refluxed with stirring at 110° C. for 2.5 hours in a mixed solvent of ethanol:N,N-dimethylformamide:chloroform (5:6:2) (3 mL). The reaction mixture was cooled to room temperature and added dropwise to ether (25 mL) to precipitate a solid, followed by filtering under reduced pressure. The obtained solid was separated and purified by column chromatography (dichloromethane/methanol) to obtain a wine-colored solid (320 mg) as a desired product.
$^1$H NMR (300 MHz, DMSO-$d_6$) δ 8.81 (d, J=4.5 Hz, 2H), 8.01 (d, J=9.2, 2.7 Hz, 2H), 7.83-7.72 (m, 6H), 7.56-7.43 (m, 8H), 6.86 (m, 2H), 6.52 (m, 2H), 6.04 (m, 2H), 5.32-5.16 (m, 4H), 5.09 (m, 2H), 4.76 (m, 2H), 4.24 (m, 2H), 4.09 (s, 6H), 3.83 (m, 2H), 3.57-3.43 (m, 2H), 3.16 (m, 2H), 3.02-2.92 (m, 2H), 2.70-2.60 (m, 2H), 2.40 (m, 4H), 1.90 (m, 2H), 1.77 (m, 2H), 1.11 (m, 2H).

Example 55. 4,4'-bis(cinchonium-N-methyl)biphenyl Sulfoxide Dibromide (27)

To a 25-mL round bottom flask, 4,4'-sulfinylbis(bromomethyl)benzene (200 mg, 0.543 mmol) was added to (−)-hydrocinchonine (272 mg, 0.924 mmol), and refluxed with stirring at 110° C. for 4.5 hours in a mixed solvent of ethanol:N,N-dimethylformamide:chloroform (5:6:2) (3 mL). The reaction mixture was cooled to room temperature and added dropwise to ether (20 mL) to precipitate a solid, followed by filtering under reduced pressure. The obtained solid was separated and purified by column chromatography (dichloromethane/methanol) to obtain a pale orange solid (388 mg) as a desired product.
$^1$H NMR (300 MHz, DMSO-$d_6$) δ 8.76 (d, J=4.5 Hz, 2H), 8.27-8.07 (m, 2H), 7.87 (m, 2H), 7.80-7.32 (m, 10H), 7.30-7.17 (m, 4H), 6.68 (m, 2H), 6.30 (m, 2H), 5.93-5.65 (m, 2H), 5.13-4.66 (m, 8H), 4.02 (m, 2H), 3.94-3.61 (m, 4H), 3.25 (m, 6H), 2.19-1.86 (m, 2H), 1.58 (m, 6H), 0.89-0.73 (m, 2H).

Example 56. 4,4'-bis(O(9)-allylcinchonium-N-methyl)biphenyl Sulfoxide Dibromide (28)

Compound 27 (50 mg, 0.052 mmol) obtained by the method of Example 55 was suspended in chloroform (2.0 mL), a 50% potassium hydroxide solution (0.15 mL, 1.32 mmol) and allyl bromide (45 mg, 0.369 mmol) were added, and then the mixture was stirred at room temperature for 1 hour. The reaction mixture was diluted with water (2 mL), and an organic layer was extracted with chloroform (2×2 mL). The chloroform solution was dried over anhydrous magnesium sulfate and filtered. The obtained solid was separated and purified by column chromatography (dichloromethane/methanol) to obtain a pale yellow solid (52 mg) as a desired product.

$^1$H NMR (300 MHz, DMSO-$d_6$) δ 9.02 (d, J=4.5 Hz, 2H), 8.40 (d, J=7.5 Hz, 2H), 8.13 (d, J=8.6 Hz, 2H), 7.90-7.71 (m, 8H), 7.57 (m, 2H), 7.53-7.37 (m, 2H), 6.39 (m, 2H), 6.17 (m, Hz, 2H), 5.99 (m, 2H), 5.44 (d, J=17.1 Hz, 3H), 5.35-5.19 (m, 7H), 4.66 (d, J=12.4 Hz, 2H), 4.28 (m, 2H), 4.14-3.92 (m, 8H), 3.57 (m, 2H), 3.03 (m, 2H), 2.82-2.60 (m, 2H), 2.43-2.29 (m, 2H), 1.93-1.70 (m, 6H), 1.21 (m, 2H).

Example 57.
4,4'-bis(cinchonium-N-methyl)biphenyl Sulfone Dibromide (29)

To a 25-mL round bottom flask, 4,4'-sulfonylbis(bromomethyl)benzene (500 mg, 1.24 mmol) was added to (+)-cinchonine (656 mg, 2.23 mmol), and refluxed with stirring at 110° C. for 4 hours in a mixed solvent of ethanol:N,N-dimethylformamide:chloroform (5:6:2) (8 mL). The reaction mixture was cooled to room temperature and added dropwise to ether (40 mL) to precipitate a solid, followed by filtering under reduced pressure. The obtained solid was separated and purified by column chromatography (dichloromethane/methanol) to obtain a pale yellow solid (321 mg) as a desired product.

$^1$H NMR (300 MHz, DMSO-$d_6$) δ 8.98 (d, J=4.5 Hz, 2H), 8.33 (d, J=8.4 Hz, 2H), 8.24 (d, J=8.1 Hz, 2H), 8.15-7.97 (m, 8H), 7.90-7.80 (m, 4H), 7.74 (m, 2H), 6.85 (m, 2H), 6.48 (m, 2H), 5.98 (m, 2H), 5.22 (m, 6H), 5.00 (m, 2H), 4.23 (m, 2H), 4.00-3.84 (m, 4H), 3.52 (m, 2H), 2.99 (m, 2H), 2.63 (m, 2H), 2.27 (m, 2H), 1.93-1.59 (m, 6H), 1.04 (m, 2H).

Example 58. 4,4'-bis(O(9)-allylcinchonium-N-methyl)biphenyl Sulfone Dibromide (30)

After Compound 29 (50 mg, 0.06 mmol) obtained by the method of Example 57 was suspended in methylene chloride (2 mL), a 50% potassium hydroxide solution (0.20 mL, 1.78 mmol) and allyl bromide (47 mg, 0.39 mmol) were added, and then the mixture was stirred at room temperature for 1 hour. The reaction mixture was diluted with water (3 mL), and an organic layer was extracted with dichloromethane (2×10 mL). The methylene chloride was dried over anhydrous magnesium sulfate and filtered, followed by vacuum evaporation. The resulting product was separated and purified by column chromatography (dichloromethane/methanol) to obtain a pale orange solid (55 mg) as a desired product.

$^1$H NMR (300 MHz, DMSO-$d_6$) δ 9.01 (d, J=4.5 Hz, 2H), 8.96 (d, J=4.5 Hz, 1H), 8.24 (d, J=8.3 Hz, 4H), 8.10 (m, 10H), 7.79 (m, 6H), 6.16 (m, 2H), 5.96 (m, 2H), 5.47-5.39 (m, 2H), 5.26 (m, 6H), 4.72 (m, 2H), 4.27 (m, 2H), 4.01 (m, 8H), 3.57 (m, 2H), 3.02 (m, 2H), 2.68 (m, 2H), 2.34 (m, 2H), 1.90 (m, 4H), 1.51 (m, 2H), 1.19 (m, 2H).

Experimental Example 1. Alkylation of N-(diphenylmethylene)glycine tert-butyl Ester under Chiral Phase-Transfer Catalytic Reaction Conditions In order to measure the efficiency of the synthesized phase-transfer catalyst, benzylation is carried out using N-(diphenylmethylene)glycine tert-butylester as a substrate as shown in Reaction Scheme 4 below. The resulting product is subjected to chiral High Performance Liquid Chromatography (HPLC) to measure optical purity. Specifically, a mixed solvent of toluene/chloroform (volume ratio=7:3, 0.75 mL) and a 50% potassium hydroxide solution (0.25 mL, 13.0 mmol) are added to N-(diphenylmethylene)glycine tert-butyl ester (30 mg, 0.102 mmol) and a chiral phase-transfer catalyst (1% eq., 0.0010 mmol), and the reaction solution was cooled to 15° C. Then, to the reaction solution, benzyl bromide (1.2 eq., 14.5 μL, 0.123 mmol) is added, and the reaction mixture is stirred at room temperature until no substrate remains. The reaction mixture is diluted with ether (20 mL), and an organic layer is washed with water, dried over anhydrous magnesium sulfate and filtered, followed by a vacuum evaporation. The obtained product is subjected to column separation (mobile phase; hexane:ethyl acetate=50:1) to obtain a colorless liquid, tert-butyl 2-(benzhydrylideneamino)-3-phenylpropionate, as a desired product. The optical purity of the obtained product is measured by asymmetric HPLC, and operating conditions of an HPLC apparatus are as follows: 1) Column: DAICEL Chiralcel OD; 2) mobile phase:hexane:2-propanol=100:1; 3) flow rate: 0.5 mL/min; 4) measuring temperature: 20° C.; 5) detector: UV spectrophotometer (254 nm); and 6) Retention time: (R)-enantiomer (minor) 12.2 min, (S)-enantiomer (major) 20.5 min.

[Reaction Scheme 4]

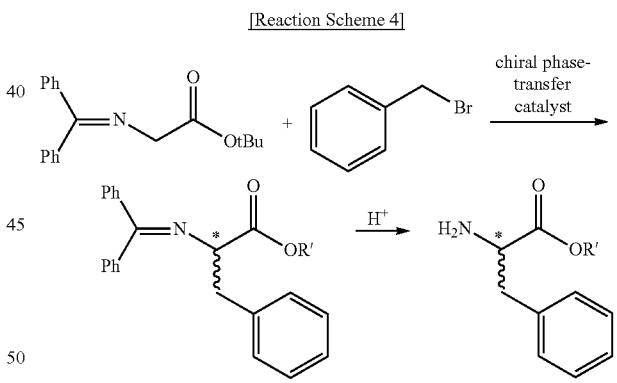

The results of the respective catalytic reactions are shown in Tables 1 and 2.

TABLE 1

| Example | Chiral Phase-Transfer Catalyst | Chemical yield (%) | Optical purity (% ee) | Enantiomer |
|---|---|---|---|---|
| 1 | 4,4'-bis(cinchonidium-N-methyl)biphenyl methanone dibromide (3) | 90 | 93 | S |
| 2 | 4,4'-bis(O(9)-allylcinchonidium-N-methyl)biphenyl methanone dibromide (4) | 93 | 96 | S |
| 3 | 4,4'-bis(hydrocinchonidium-N-methyl)biphenyl methanone dibromide (3-1) | 82 | 96 | S |

TABLE 1-continued

| Example | Chiral Phase-Transfer Catalyst | Chemical yield (%) | Optical purity (% ee) | Enantiomer |
|---|---|---|---|---|
| 4 | 4,4'-bis(O(9)-allylhydrocinchonidium-N-methyl)biphenyl methanone dibromide (4-1) | 89 | 97 | S |
| 5 | 3,4'-bis(cinchonidium-N-methyl)biphenyl methanone dibromide (3-2) | 61 | 87 | S |
| 6 | 3,4'-bis(O(9)-allylcinchonidium-N-methyl)biphenyl methanone dibromide (4-2) | 89 | 89 | S |
| 7 | 3,3'-bis(cinchonidium-N-methyl)biphenyl methanone dibromide (3-3) | 79 | 64 | S |
| 8 | 3,3'-bis(O(9)-allylcinchonidium-N-methyl)biphenyl methanone dibromide (4-3) | 84 | 71 | S |
| 9 | 4,4'-bis(cinchonidium-N-methyl)biphenyl methane dibromide (5) | 89 | 96 | S |
| 10 | 4,4'-bis(O(9)-allylcinchonidium-N-methyl)biphenylmethane dibromide (6) | 93 | 98 | S |
| 11 | 4,4'-bis(hydrocinchonidium-N-methyl)biphenyl methane dibromide (5-1) | 82 | 97 | S |
| 12 | 4,4'-bis(O(9)-allylhyddrocinchonidium-N-methyl)biphenylmethane dibromide (6-1) | 93 | 98 | S |
| 13 | 4,4'-bis(quinium-N-methyl)biphenyl methane dibromide (5-2) | 92 | 73 | S |
| 14 | 4,4'-bis(O(9)-allylquinium-N-methyl)biphenylmethane dibromide (6-2) | 78 | 79 | S |
| 15 | 4,4'-bis(cinchonidium-N-methyl)biphenyl methanol dibromide (7) | 67 | 88 | S |
| 16 | 4,4'-bis(O(9)-allylcinchonidium-N-methyl)biphenylmethanol dibromide (8) | 65 | 92 | S |
| 17 | 4,4'-bis(hydrocinchonidium-N-methyl)biphenyl methanol dibromide (7-1) | 81 | 92 | S |
| 18 | 4,4'-bis(O(9)-allylhydrocinchonidium-N-methyl)biphenylmethanol dibromide (8-1) | 64 | 94 | S |
| 19 | 4,4'-bis(cinchonidium-N-methyl)biphenyl ether dibromide (9) | 88 | 95 | S |
| 19-1 | 3,3'-bis(cinchonidium-N-methyl)biphenyl ether dibromide (9-1) | 78 | 83 | S |
| 20 | 4,4'-bis(O(9)-allylcinchonidium-N-methyl)biphenyl ether dibromide (10) | 92 | 97 | S |
| 20-1 | 3,3'-bis(O(9)-allylcinchonidium-N-methyl)biphenyl ether dibromide (10-1) | 95 | 93 | S |
| 21 | 4,4'-bis(O(9)-benzylcinchonidium-N-methyl)biphenyl ether dibromide (10-1-1) | 95 | 93 | S |
| 22 | 4,4'-bis(hydrocinchonidium-N-methyl)biphenyl ether dibromide (9-2) | 95 | 95 | S |
| 23 | 4,4'-bis(O(9)-allylhydrocinchonidium-N-methyl)biphenyl ether dibromide (10-2) | 95 | 98 | S |
| 24 | 4,4'-bis(quinium-N-methyl)biphenyl ether dibromide (9-3) | 86 | 73 | S |
| 25 | 4,4'-bis(O(9)-allylquinum-N-methyl)biphenyl ether dibromide (10-3) | 88 | 74 | S |
| 26 | 4,4'-bis(cinchonidium-N-methyl)biphenyl thioether dibromide (11) | 85 | 97 | S |
| 26-1 | 3,3'-bis(cinchonidium-N-methyl)biphenyl sulfide dibromide (11-1) | 89 | 67 | S |
| 27 | 4,4'-bis(O(9)-allylcinchonidium-N-methyl)biphenyl thioether dibromide (12) | 86 | 98 | S |

TABLE 1-continued

| Example | Chiral Phase-Transfer Catalyst | Chemical yield (%) | Optical purity (% ee) | Enantiomer |
|---|---|---|---|---|
| 27-1 | 3,3'-bis(O(9)-allylcinchonidium-N-methyl)biphenyl sulfide dibromide (12-1) | 82 | 78 | S |
| 28 | 4,4'-bis(hydrocinchonidium-N-methyl)biphenyl thioether dibromide (11-2) | 96 | 98 | S |
| 29 | 4,4'-bis(O(9)-allylhydrocinchonidium-N-methyl)biphenyl thioether dibromide (12-2) | 95 | 99 | S |
| 30 | 4,4'-bis(quinium-N-methyl)biphenyl thioether dibromide (11-3) | 70 | 83 | S |
| 31 | 4,4'-bis(O(9)-allylquinium-N-methyl)biphenyl thioether dibromide (12-3) | 95 | 87 | S |
| 32 | 4,4'-bis(cinchonidium-N-methyl)biphenyl sulfoxide dibromide (13) | 95 | 97 | S |
| 33 | 4,4'-bis(O(9)-allylcinchonidium-N-methyl)biphenyl sulfoxide dibromide (14) | 87 | 98 | S |
| 34 | 4,4'-bis(hydrocinchonidium-N-methyl)biphenyl sulfoxide dibromide (13-1) | 92 | 97 | S |
| 35 | 4,4'-bis(O(9)-allylhydrocinchonidium-N-methyl)biphenyl sulfoxide dibromide (14-1) | 85 | 98 | S |
| 36 | 4,4'-bis(cinchonidium-N-methyl)biphenyl sulfone dibromide (15) | 90 | 94 | S |
| 37 | 4,4'-bis(O(9)-allylcinchonidium-N-methyl)biphenyl sulfone dibromide (16) | 77 | 95 | S |
| 38 | 4,4'-bis(hydrocinchonidium-N-methyl)biphenyl sulfone dibromide (15-1) | 92 | 95 | S |
| 39 | 4,4'-bis(O(9)-allylhydrocinchonidium-N-methyl)biphenyl sulfone dibromide (16-1) | 91 | 98 | S |
| Comparative Example 1 | N-benzyl-cinchonidium chloride | 91 | 79 | S |
| Comparative Example 2 | N-benzyl-O(9)-allylcinchonidium bromide | 94 | 81 | S |

(Comparative Example 1, 2: O'Donnell, M. J.; Bennett, W. D.; Wu, S. J. Am. Chem. Soc. 1989, 111, 2353.)

TABLE 2

| Example | Chiral phase-transfer Catalyst | Chemical yield (%) | Optical purity (% ee) | Enantiomer |
|---|---|---|---|---|
| 40 | 4,4'-bis(cinchonium-N-methyl)biphenyl methanone dibromide (17) | 84 | 88 | R |
| 41 | 4,4'-bis(O(9)-allylcinchonium-N-methyl)bipheny lmethanone dibromide (18) | 82 | 92 | R |
| 42 | 4,4'-bis(cinchonium-N-methyl)biphenyl methane dibromide (19) | 90 | 87 | R |
| 43 | 4,4'-bis(O(9)-allylcinchonium-N-methyl)biphenylmethane dibromide (20) | 95 | 92 | R |
| 44 | 4,4'-bis(quinidium-N-methyl)biphenyl methane dibromide (19-1) | 90 | 64 | R |
| 45 | 4,4'-bis(O(9)-allylquinidium-N-methyl)biphenylmethane dibromide (20-1) | 77 | 81 | R |
| 46 | 4,4'-bis(cinchonium-N-methyl)biphenyl methanol dibromide (21) | 92 | 88 | R |

TABLE 2-continued

| Example | Chiral phase-transfer Catalyst | Chemical yield (%) | Optical purity(% ee) | Enantiomer |
|---|---|---|---|---|
| 47 | 4,4'-bis(O(9)-allylcinchonium-N-methyl)biphenylmethanol dibromide (22) | 89 | 90 | R |
| 48 | 4,4'-bis(cinchonium-N-methyl)biphenyl ether dibromide (23) | 82 | 88 | R |
| 49 | 4,4'-bis(O(9)-allylcinchonium-N-methyl)biphenyl ether dibromide (24) | 98 | 95 | R |
| 50 | 4,4'-bis(quinidium-N-methyl)biphenyl ether dibromide (23-1) | 83 | 74 | R |
| 51 | 4,4'-bis(O(9)-allylquinidium-N-methyl)biphenyl ether dibromide (24-1) | 81 | 83 | R |
| 52 | 4,4'-bis(cinchonium-N-methyl)biphenyl thioether dibromide (25) | 92 | 86 | R |
| 53 | 4,4'-bis(O(9)-allylcinchonium-N-methyl)biphenyl thioether dibromide (26) | 80 | 95 | R |
| 54 | 4,4'-bis(quinidium-N-methyl)biphenyl thioether dibromide (25-1) | 92 | 72 | R |
| 55 | 4,4'-bis(cinchonium-N-methyl)biphenyl sulfoxide dibromide (27) | 91 | 83 | R |
| 56 | 4,4'-bis(O(9)-allylcinchonium-N-methyl)biphenyl sulfoxide dibromide (28) | 95 | 93 | R |
| 57 | 4,4'-bis(cinchonium-N-methyl)biphenyl sulfone dibromide (29) | 84 | 80 | R |
| 58 | 4,4'-bis(O(9)-allylcinchonium-N-methyl)biphenyl sulfone dibromide (30) | 97 | 90 | R |
| Comparative Example 3 | N-benzyl-cinchonium chloride | 75 | 66 | R |
| Comparative Example 4 | N-benzyl-O(9)-allylcinchonium bromide | 84 | 70 | R |

(Comparative Example 3: O'Donnell, M. J.; Bennett, W. D.; Wu, S. J. Am. Chem. Soc. 1989, 111, 2353.

Comparative Example 4: O'Donnell, M. J.; Wu, S.; Esikova, I.; Mi, A. WO 9506029A1 19950302)

As shown in Tables 1 and 2, the monobenzyl ammonium catalysts (10% eq.) of Comparative Examples 1 and 2 exhibited (S)-optical purity of 80% ee, whereas the catalysts of the present invention exhibited a high optical purity of 95 to 99% ee under conditions of 1% eq. catalyst and 1.2 eq. benzyl bromide. In addition, the monobenzyl ammonium catalysts (10% eq.) of Comparative Examples 3 and 4 exhibited (R)-optical purity of about 70% ee. On the other hand, the catalysts of the present invention exhibited high optical purity of the maximum of 95% ee under conditions of 1% eq. catalyst and 1.2 eq. benzyl bromide. From the above results, the catalysts of the present invention exhibited high optical purity with only a low catalyst amount and the application of almost equivalent amount of a reagent and may be prepared by a simple process, and thus it can be seen that the catalysts may be widely applied in preparation of alpha-amino acids on the industrial level.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A cinchona-alkaloid compound of Formula 1 below:

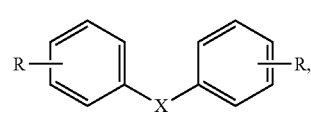

[Formula 1]

wherein,

X is selected from the group consisting of —CH$_2$—, —C(OH)H—, —C(=O)—, —O—, —S—, and —S(=O)—;

R is

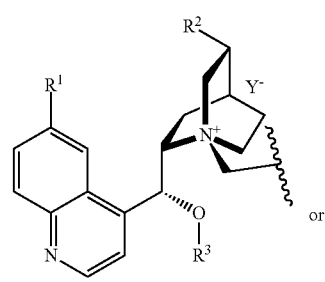

or

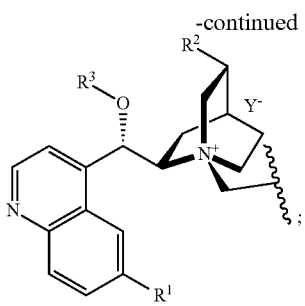

R¹ is selected from the group consisting of hydrogen, $C_1$ to $C_{10}$ alkyl, and $C_1$ to $C_5$ alkoxy;
R² is vinyl or ethyl;
R³ is selected from the group consisting of hydrogen, $C_1$ to $C_{10}$ alkyl, allyl, $C_5$ to $C_{10}$ aryl, naphthalen-1-yl-methyl, and anthracen-9-yl-methyl; and
Y⁻ is selected from the group consisting of: halogen anion of fluoride, chloride, bromide, and iodide, $IO_4^-$, $ClO_4^-$, $R^4SO_3^-$, trifluoromethane sulfonate (OTf⁻) and $HSO_4^-$, wherein R⁴ is $C_1$-$C_4$ alkyl or $C_5$-$C_0$ aryl.

2. The compound according to claim 1, wherein said X of the compound of Formula 1 is one of —$CH_2$—, —C(OH)H— or —C(═O)—, wherein
R¹ is hydrogen or $C_1$ to $C_5$ alkoxy;
R² is vinyl or ethyl;
R³ is hydrogen, $C_1$ to $C_{10}$ alkyl, allyl, or $C_5$ to $C_{10}$ aryl; and
Y⁻ is halogen anion selected from the group consisting of fluorine, chlorine, bromine, and iodine.

3. The compound according to claim 1, wherein said X of the compound of Formula 1 is —$CH_2$—, —C(OH)H— or —C(═O)—, wherein
R¹ is hydrogen or methoxy group;
R² is vinyl or ethyl group;
R³ is hydrogen or allyl group; and
Y⁻ is halogen anion selected from the group consisting of fluoride, chloride, bromide, and iodide.

4. The compound according to claim 3, wherein said compound is selected from the group consisting of:
4,4'-bis(cinchonidium-N-methyl)biphenyl methanone dibromide;
4,4'-bis(O(9)-allylcinchonidium-N-methyl)biphenyl methanone dibromide;
4,4'-bis(hydrocinchonidium-N-methyl)biphenyl methanone dibromide;
4,4'-bis(O(9)-allylhydrocinchonidium-N-methyl)biphenyl methanone dibromide;
3,4'-bis(cinchonidium-N-methyl)biphenyl methanone dibromide;
3,4'-bis(O(9)-allylcinchonidium-N-methyl)biphenyl methanone dibromide;
3,3'-bis(cinchonidium-N-methyl)biphenyl methanone dibromide;
3,3'-bis(O(9)-allylcinchonidium-N-methyl)biphenyl methanone dibromide;
4,4'-bis(cinchonidium-N-methyl)biphenyl methane dibromide;
4,4'-bis(O(9)-allylcinchonidium-N-methyl)biphenyl methane dibromide;
4,4'-bis(hydrocinchonidium-N-methyl)biphenyl methane dibromide,
4,4'-bis(O(9)-allylhydrocinchonidium-N-methyl)biphenyl methane dibromide;
4,4'-bis(quinium-N-methyl)biphenyl methane dibromide;
4,4'-bis(O(9)-allylquinium-N-methyl)biphenyl methane dibromide;
4,4'-bis(cinchonidium-N-methyl)biphenyl methanol dibromide;
4,4'-bis(O(9)-allylcinchonidium-N-methyl)biphenyl methanol dibromide,
4,4'-bis(hydrocinchonidium-N-methyl)biphenyl methanol dibromide;
4,4'-bis(O(9)-allylhydrocinchonidium-N-methyl)biphenyl methanol dibromide,
4,4'-bis(cinchonium-N-methyl)biphenyl methanone dibromide,
4,4'-bis(O(9)-allylcinchonium-N-methyl)biphenyl methanone dibromide,
4,4'-bis(cinchonium-N-methyl)biphenyl methane dibromide,
4,4'-bis(O(9)-allylcinchonium-N-methyl)biphenyl methane dibromide;
4,4'-bis(quinidium-N-methyl)biphenyl methane dibromide;
4,4'-bis(O(9)-allylquinidium-N-methyl)biphenyl methane dibromide;
4,4'-bis(cinchonium-N-methyl)biphenyl methanol dibromide; and
4,4'-bis(O(9)-allylcinchonium-N-methyl)biphenyl methanol dibromide.

5. The compound according to claim 1, wherein said X of the compound of Formula 1 is —O—, —S— or —S(═O)—, wherein
R¹ is hydrogen or $C_1$-$C_5$ alkoxy;
R² is vinyl or ethyl;
R³ is hydrogen, $C_1$-$C_{10}$ alkyl, allyl, or $C_5$-$C_{10}$ aryl; and
Y⁻ is halogen anion selected from the group consisting of fluorine, chlorine, bromine, and iodine.

6. The compound according to claim 1, wherein said X of the compound of Formula 1 is —O—, —S— or —S(═O)—, wherein
R¹ is hydrogen or methoxy;
R² is vinyl or ethyl;
R³ is hydrogen, allyl, or benzyl; and
Y⁻ is halogen anion selected from the group consisting of fluorine, chlorine, bromine, and iodine.

7. The compound according to claim 6, wherein said compound is selected from the group consisting of:
4,4'-bis(cinchonidium-N-methyl)biphenyl ether dibromide;
4,4'-bis(O(9)-allylcinchonidium-N-methyl)biphenyl ether dibromide;
4,4'-bis(O(9)-benzyl-cinchonidium-N-methyl)biphenyl ether dibromide;
4,4'-bis(hydrocinchonidium-N-methyl)biphenyl ether dibromide;
4,4'-bis(O(9)-allylhydrocinchonidium-N-methyl)biphenyl ether dibromide;
4,4'-bis(quinium-N-methyl)biphenyl ether dibromide;
4,4'-bis(O(9)-allylquinium-N-methyl)biphenyl ether dibromide;
3,3'-bis(cinchonidium-N-methyl)biphenyl ether dibromide;
3,3'-bis(O(9)-allylcinchonidium-N-methyl)biphenyl ether dibromide;
4,4'-bis(cinchonidium-N-methyl)biphenyl thioether dibromide;
4,4'-bis(O(9)-allylcinchonidium-N-methyl)biphenyl thioether dibromide;

4,4'-bis(hydrocinchonidium-N-methyl)biphenyl thioether dibromide;
4,4'-bis(O(9)-allylhydrocinchonidium-N-methyl)biphenyl thioether dibromide;
4,4'-bis(quinium-N-methyl)biphenyl thioether dibromide;
4,4'-bis(O(9)-allylquinium-N-methyl)biphenyl thioether dibromide;
3,3'-bis(cinchonidium-N-methyl)biphenyl sulfide dibromide;
3,3'-bis(O(9)-allylcinchonidium-N-methyl)biphenyl sulfide dibromide;
4,4'-bis(cinchonidium-N-methyl)biphenyl sulfoxide dibromide;
4,4'-bis(O(9)-allylcinchonidium-N-methyl)biphenyl sulfoxide dibromide;
4,4'-bis(hydrocinchonidium-N-methyl)biphenyl sulfoxide dibromide;
4,4'-bis(O(9)-allylhydrocinchonidium-N-methyl)biphenyl sulfoxide dibromide;
4,4'-bis(cinchonium-N-methyl)biphenyl ether dibromide;
4,4'-bis(O(9)-allylcinchonium-N-methyl)biphenyl ether dibromide;
4,4'-bis(quinidium-N-methyl)biphenyl ether dibromide;
4,4'-bis(O(9)-allylquinidium-N-methyl)biphenyl ether dibromide;
4,4'-bis(cinchonium-N-methyl)biphenyl thioether dibromide;
4,4'-bis(O(9)-allylcinchonium-N-methyl)biphenyl thioether dibromide;
4,4'-bis(quinidium-N-methyl)biphenyl thioether dibromide;
4,4'-bis(cinchonium-N-methyl)biphenyl sulfoxide dibromide; and
4,4'-bis(O(9)-allylcinchonium-N-methyl)biphenyl sulfoxide dibromide.

* * * * *